United States Patent
Pelzer et al.

(10) Patent No.: US 12,234,206 B2
(45) Date of Patent: Feb. 25, 2025

(54) BI- AND TRICYCLIC COMPOUNDS FOR USE AS AROMA CHEMICALS

(71) Applicants: BASF SE, Ludwigshafen am Rhein (DE); P2 Science Inc., Woodbridge (DE)

(72) Inventors: Ralf Pelzer, Lampertheim (DE); Yonghua Yang, Woodbridge, CT (US); Patrick Foley, Woodbridge, CT (US)

(73) Assignees: BASF SE, Ludwigshafen am Rhein (DE); P2 Science Inc., Woodbridge, CT (US)

( * ) Notice: Subject to any disclaimer, the term of this patent is extended or adjusted under 35 U.S.C. 154(b) by 749 days.

(21) Appl. No.: 17/414,666

(22) PCT Filed: Dec. 17, 2019

(86) PCT No.: PCT/EP2019/085701
§ 371 (c)(1),
(2) Date: Jun. 16, 2021

(87) PCT Pub. No.: WO2020/127305
PCT Pub. Date: Jun. 25, 2020

(65) Prior Publication Data
US 2022/0064095 A1    Mar. 3, 2022

(30) Foreign Application Priority Data
Dec. 18, 2018  (EP) ..................... 18213459

(51) Int. Cl.
*C07C 49/323* (2006.01)
*C07C 49/553* (2006.01)

(52) U.S. Cl.
CPC ......... *C07C 49/323* (2013.01); *C07C 49/553* (2013.01); *C07C 2602/28* (2017.05); *C07C 2603/68* (2017.05)

(58) Field of Classification Search
CPC . C07C 49/323; C07C 49/553; C07C 2602/28; C07C 2603/68; C07C 49/313
(Continued)

(56) References Cited

FOREIGN PATENT DOCUMENTS

| EP | 1070699 A1 | 1/2001 |
|---|---|---|
| WO | 2013/092781 A1 | 6/2013 |
| WO | 2018/185010 A1 | 10/2018 |

OTHER PUBLICATIONS

Baddeley et al., "The Interaction of Decalin and Friedel-Crafts Acetylating Agent", Journal of the chemical society, Jan. 1, 1959, pp. 1324-1327.
(Continued)

*Primary Examiner* — Ana Z Muresan
(74) *Attorney, Agent, or Firm* — Faegre Drinker Biddle & Reath LLP

(57) ABSTRACT

The present invention relates to bi- and tricyclic compounds of the general formula (I) (I) wherein the dashed lines independently of each other represent a single or a double bond, X represents a group of the formulae $X_1$ to $X_3$ wherein the asterisk denotes the point of attachment to the rest of the molecule, $R^{1a}$ and $R^{1b}$, independently of each other, are selected from hydrogen or methyl, or $R^{1a}$ together with $R^{1b}$ form a methylene or ethylene group, $R^2$, $R^{3a}$, $R^{3b}$, $R^4$, $R^{5a}$ and $R^{5b}$, independently of each other, are selected from hydrogen or methyl, $R^6$ is selected from hydrogen, methyl or ethyl, and $R^7$ is methyl or ethyl, to a method of preparing said compounds, to the use of a bi- or tricyclic compounds or of mixtures of two or more bi- and tricyclic compounds or of a stereoisomer thereof or of a mixture of two or more stereoisomers thereof as aroma chemicals; to the use of a bi- or tricyclic compound for modifying the scent character of a fragranced composition; to an aroma chemical composition containing a bi- or tricyclic compound or a mixture of two or more bi- and tricyclic compounds or of a stereoisomer thereof or of a mixture of two or more stereoisomers thereof; and to a method of preparing a fragranced composition or for modifying the scent character of a fragranced composition, comprising incorporating a bi- or tricyclic compound or a mixture of two or more bi- and tricyclic compounds or of a stereoisomer thereof or of a mixture of two or more stereoisomers thereof into said composition.

11 Claims, No Drawings

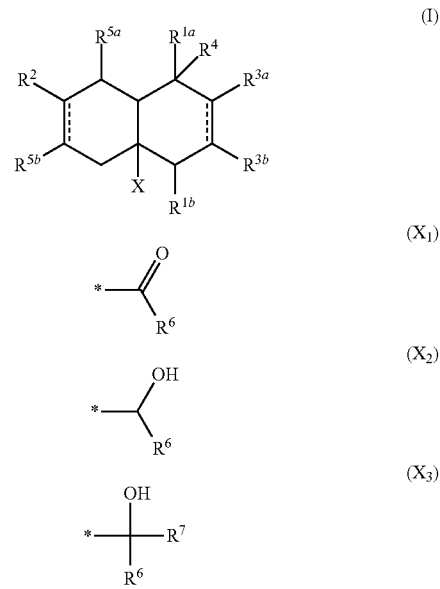

(58) Field of Classification Search
USPC .......................................................... 568/328
See application file for complete search history.

(56) References Cited

OTHER PUBLICATIONS

Baddeley et al., "The Preparation of Novel Decalin Derivatives from Lobeta-(1,2-Dihydroxyethyl)-Trans-Lbeta-De Calol", Journal of the chemical society, Jan. 1, 1961, pp. 3838-3842.
Bergmann et al., "Diels-Alder Reactions with 1-Formylcyclohexene and 1-Formylcyclopentene", Journal of The American Chemical Society, vol. 81, No. 1, Jan. 1, 1959, pp. 221-225.
Hayashi et al., "A Novel Chiral Super-Lewis Acidic Catalyst for Enantioselective Synthesis", Journal of the chemical society, vol. 118, No. 23, Jun. 12, 1996, pp. 5502-5503.
International Preliminary Report on Patentability received for PCT Patent Application No. PCT/EP2019/085701, mailed on Jul. 1, 2021, 9 pages.
International Search Report and Written Opinion received for PCT Patent Application No. PCT/EP2019/085701, mailed on Feb. 14, 2020, 12 pages.
Lee et al., "An ionic Diets-Alder route to cis-fused octalins containing an all-carbon quaternary stereocenter in an angular position", Tetrahedron Letters, vol. 51, No. 9, Mar. 3, 2010, pp. 1252-1253.
Liu et al., "The Total Synthesis of Racemic Isoacanthodoral", J. Chem. Soc., chem. Commun, Jan. 1, 1990, pp. 1419-1421.
Lyall et al., "Aliphatic C—H activation with a luminium trichloride-acetyl chloride: expanding the scope of the Baddeley reaction for the functionalisation of saturated hydrocarbons", Organic & Biomolecular Chemistry, vol. 11, No. 9, Jan. 1, 2013, pp. 1468-1475.

BI- AND TRICYCLIC COMPOUNDS FOR USE AS AROMA CHEMICALS

CROSS-REFERENCE TO RELATED APPLICATIONS

This application is a national stage application (under 35 U.S.C. § 371) of PCT/EP2019/085701, filed Dec. 17, 2019, which claims benefit of European Application No. 18213459.3, filed Dec. 18, 2018, both of which are incorporated herein by reference in their entirety.

The present invention relates to bi- and tricyclic compounds of the formula (I) as described herein, in particular bi- and tricyclic ketones, to a method of preparing said compounds, to the use of a bi- or tricyclic compounds or of mixtures of two or more bi- and tricyclic compounds or of a stereoisomer thereof or of a mixture of two or more stereoisomers thereof as aroma chemicals; to the use of a bi- or tricyclic compound for modifying the scent character of a fragranced composition; to an aroma chemical composition containing a bi- or tricyclic compound or a mixture of two or more bi- and tricyclic compounds or of a stereoisomer thereof or of a mixture of two or more stereoisomers thereof; and to a method of preparing a fragranced composition or for modifying the scent character of a fragranced composition, comprising incorporating a bi- or tricyclic compound or a mixture of two or more bi- and tricyclic compounds or of a stereoisomer thereof or of a mixture of two or more stereoisomers thereof into said composition.

TECHNICAL BACKGROUND

Aroma chemicals, especially fragrances, are of great interest especially in the field of cosmetics and cleaning and laundry compositions. Fragrances of natural origin are mostly expensive, often limited in their available amount and, on account of fluctuations in environmental conditions, are also subject to variations in their content, purity etc. To circumvent these undesirable factors, it is therefore of great interest to create synthetic substances which have organoleptic properties that resemble more expensive natural fragrances or which have novel and interesting organoleptic profiles.

Despite a large number of already existing synthetic aroma chemicals (fragrances and flavorings), there is a constant need for new components in order to be able to satisfy the multitude of properties desired for extremely diverse areas of application. These include, firstly, the organoleptic properties, i.e. the compounds should have advantageous odiferous (olfactory) or gustatory properties. Furthermore, aroma chemicals should also have additional positive secondary properties, such as e.g. an efficient preparation method, the possibility of providing better sensory profiles as a result of synergistic effects with other fragrances, a higher stability under certain application conditions, a higher extendability, a better higher substantivity, etc.

However, since even small changes in chemical structure bring about massive changes in the sensory properties such as odor and also taste, the targeted search for substances with certain sensory properties such as a certain odor is extremely difficult.

The search for new fragrances and flavorings is therefore in most cases difficult and laborious without knowing whether a substance with the desired odor and/or taste will even actually be found.

E. D. Bergmann et al., J. Am. Chem. Soc. 81 (1959), 221-225, describe Diels-Alder reactions with 1-formylcyclohexene. One of the reaction products is 6,7-dimethyl-2,3,4,5,8,8a-hexahydro-1H-naphthalene-4a-carbaldehyde.

Hsing-Jang Liu et al., J. Chem. Soc., Chem. Commun., 1990, 1419-1421, describe the total synthesis of racemic Isoacanthodoral. One of the side products formed in the total synthesis is (3,8,8-trimethyl-1,4,5,6,7,8a-hexahydronaphthalene-4a-yl)methanol.

EP1070699 describes alicyclic compounds containing a hydroxymethyl group and the use of the same for producing polymerizable compounds. One of the hydroxymethyl compounds is 2-decalin-4a-ylpropan-2-ol.

G. Baddeley et al., J. Chem. Soc. 1961, 3838-3842, describe the preparation of decaline derivatives from 10β-(1,2-dihydroxyethyl)-trans-1β-decalol. They describe inter alia 1-decalin-4a-ylethan-1-ol and decalin-4a-ylcarbaldehyde.

G. Baddeley et al. J. Chem. Soc. 1959, 1324-1327, describe the reaction of decaline in a Friedl-Crafts reaction. One of the derivatives formed is 9-acetyl-trans-decalin, i.e. 2-decalin-4a-ylethanone. A similar reaction was described by C. L. Lyall et al., Org. Biomol. Chem., 11 (2013), 1468-1475.

Y. Hayashi et al., J. Am. Chem. Soc. 118 (1996), 5502-5503, describe a chiral Super-Lewis acidic catalyst for enantioselective synthesis. Using this catalyst in the reaction of cyclohexene-1-carbaldehyde with cyclopentadiene yields tricyclo[4.4.1$^{2,5}$.0$^{1,6}$]undeca-3-en-1-carbaldehyde.

J. H. Lee et al., Tetrahedron Letters 51 (2010) 1252-1253, describe a ionic Diels-Alder reaction of 2-(cyclohexen-1-yl)-1,3-dioxolane with 1- or 2-methylbutadiene or 2,3-dimethylbutadiene to yield 5-methyl-2,3,4,5,8,8a-hexahydro-1H-naphthalene-4a-carbaldehyde, 7-methyl-2,3,4,5,8,8a-hexahydro-1H-naphthalene-4a-carbaldehyde or 6,7-dimethyl-2,3,4,5,8,8a-hexahydro-1H-naphthalene-4a-carbaldehyde.

None of these references suggests that these compounds may be useful as aroma chemicals.

It is the object of the present invention to provide new aroma chemicals. These should have pleasant organoleptic properties. It was a further object of the present invention to provide substances which can be used as an aroma chemical in ready-to-use compositions. In particular, odor-intensive substances, which have a pleasant odor and/or which can provide other sensual effects, such as cooling are sought. Furthermore, they should be combinable with other aroma chemicals, allowing the creation of novel advantageous sensory profiles. In addition, these aroma chemicals should be obtainable from readily available starting materials, allowing their fast and economic manufacturing, and should be free of toxicological concerns.

This object is achieved by the compound of formula (I) as shown below or mixtures thereof or stereoisomers thereof.

SUMMARY OF THE INVENTION

The invention relates to compounds of the general formula (I)

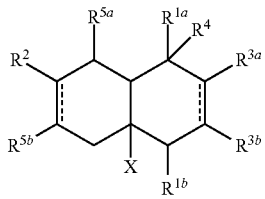
(I)

wherein
the dashed lines independently of each other represent a single or a double bond,
X represents a group of the formulae $X_1$ to $X_3$

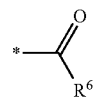
($X_1$)

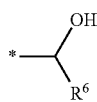
($X_2$)

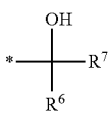
($X_3$)

wherein the asterisk denotes the point of attachment to the rest of the molecule,
$R^{1a}$ and $R^{1b}$, independently of each other, are selected from hydrogen or methyl, or $R^{1a}$ together with $R^{1b}$ form a methylene or ethylene group,
$R^2$, $R^{3a}$, $R^{3b}$, $R^4$, $R^{5a}$ and $R^{5b}$, independently of each other, are selected from hydrogen or methyl,
$R^6$ is selected from hydrogen, methyl or ethyl, and
$R^7$ is selected methyl or ethyl.

The present invention also relates to the stereoisomers of compounds of the general formula (I), to mixtures of compounds of the formula (I) and to mixtures of stereoisomers of the compounds of the formula (I).

One aspect of the invention relates to compounds of the general formula (I), to mixtures of compounds of the formula (I) and to mixtures of stereoisomers of the compounds of the formula (I), except for the following compounds: 6,7-dimethyl-2,3,4,5,8,8a-hexahydro-1H-naphthalene-4a-carbaldehyde, (3,8,8-trimethyl-1,4,5,6,7,8a-hexahydronaphthalene-4a-yl)methanol, 2-decalin-4a-ylpropan-2-ol, 1-decalin-4a-ylethan-1-ol, decalin-4a-ylcarbaldehyde, 2-decalin-4a-ylethanone, tricyclo[4.4.1$^{2,5}$.0$^{1,6}$]undeca-3-en-1-carbaldehyde, 5-methyl-2,3,4,5,8,8a-hexahydro-1H-naphthalene-4a-carbaldehyde, 7-methyl-2,3,4,5,8,8a-hexahydro-1H-naphthalene-4a-carbaldehyde and 6,7-dimethyl-2,3,4,5,8,8a-hexahydro-1H-naphthalene-4a-carbaldehyde.

Another aspect of the invention relates to a process for preparing a compound of the general formula (I), or a mixture of two or more compounds of the general formula (I) or a stereoisomer thereof or a mixture of two or more stereoisomers thereof, which method comprises:
(i) reacting a compound of the general formula (II)

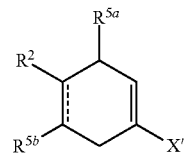
(II)

wherein
the dashed line represent a single or a double bond,
X' represents a group of the formula $X_1$

($X_1$)

wherein the asterisk denotes the point of attachment to the rest of the molecule,
$R^2$, $R^{5a}$ and $R^{5b}$, independently of each other, are selected from hydrogen or methyl, and
$R^6$ is selected from hydrogen, methyl or ethyl,
with a diene compound of the general formula (III)

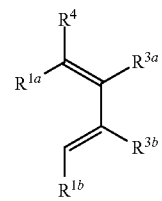
(III)

wherein
$R^{1a}$ and $R^{1b}$, independently of each other, are selected from hydrogen or methyl,
or $R^{1a}$ together with $R^{1b}$ form a methylene or ethylene group, and
$R^{3a}$, $R^{3b}$ and $R^4$, independently of each other, are selected from hydrogen or methyl,
in the presence of a catalyst,
to yield a compound of the general formula (I), where the dashed line between the carbon atoms carrying the radicals $R^{3a}$ and $R^{3b}$ is a double bond and X represents a group $X_1$,
and optionally one or two of the following steps:
(ii.a) selective catalytic hydrogenating of the C=C double bond(s) of the compound obtained in step (i) with hydrogen in the presence of a hydrogenation catalyst, to obtain a compound of the general formula (I), wherein the dashed lines represent single bonds and X represents a group $X_1$,
or
(ii.b) catalytic hydrogenation of the C=C double bond(s) and the C=O double bond of the compound obtained in step (i) with hydrogen in the presence of a hydrogenation catalyst, to obtain a compound of the general formula (I), wherein the dashed lines represent single bonds and X represents a group $X_2$, (iii.a) subjecting the compound obtained in step (i) or the compound obtained in step (ii.a) to a reduction reaction of the carbonyl group to a hydroxyl group, to obtain a compound of the general formula (I), wherein the dashed lines independently of each other represent a single or a double bond and X represents a group $X_2$, or (iii.b) reacting the compound obtained in step (i) or the compound obtained in step (ii.a) with a methyl nucleophile or an ethyl nucleophile, to obtain a compound of the general formula (I), where the dashed lines independently of each other represent a single or a double bond and X represents a group $X_3$.

This method is also termed method A.

A further aspect of the invention relates to a process for preparing a compound of the general formula (I), or a mixture of two or more compounds of the general formula (I) or a stereoisomer thereof or a mixture of two or more stereoisomers thereof, which method comprises:

(i') reacting a compound of the general formula (II')

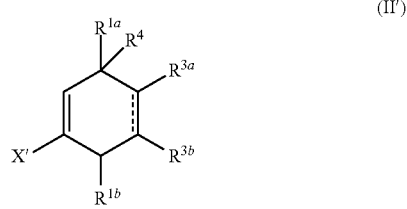

(II')

wherein
the dashed line represent a single or a double bond,
X' represents a group of the formula $X_1$

($X_1$)

wherein the asterisk denotes the point of attachment to the rest of the molecule, $R^{1a}$ and $R^{1b}$, independently of each other, are selected from hydrogen or methyl, or $R^{1a}$ together with $R^{1b}$ form a methylene or ethylene group, and $R^{3a}$, $R^{3b}$ and $R^4$, independently of each other, are selected from hydrogen or methyl, $R^6$ is selected from hydrogen, methyl or ethyl, with a diene compound of the general formula (III')

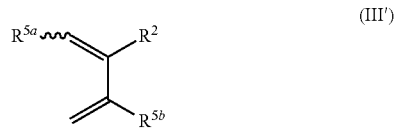

(III')

wherein
$R^2$, $R^{5a}$ and $R^{5b}$, independently of each other, are selected from hydrogen or methyl, in the presence of a catalyst, to yield a compound of the general formula (I), where the dashed line between the carbon atoms carrying the radicals $R^2$ and $R^{5b}$ is a double bond and X represents a group $X_1$, and optionally one or two of the following steps:

(ii'.a) selective catalytic hydrogenation of the C=C double bond(s) of the compound obtained in step (i') with hydrogen in the presence of a hydrogenation catalyst, to obtain a compound of the general formula (I), wherein the dashed lines represent single bonds and X represents a group $X_1$, or (ii'.b) catalytic hydrogenation of the C=C double bond(s) and the C=O double bond of the compound obtained in step (i') with hydrogen in the presence of a hydrogenation catalyst, to obtain a compound of the general formula (I), wherein the dashed lines represent single bonds and X represents a group $X_2$, (iii'.a) subjecting the compound obtained in step (i') or the compound obtained in step (ii'.a) to a reduction reaction of the carbonyl group to a hydroxyl group, to obtain a compound of the general formula (I), wherein the dashed lines independently of each other represent a single or a double bond and X represents a group $X_2$, or (iii'.b) reacting the compound obtained in step (i') or the compound obtained in step (ii'.a) with a methyl nucleophile or an ethyl nucleophile, to obtain a compound of the general formula (I), where the dashed lines independently of each other represent a single or a double bond and X represents a group $X_3$.

This method is also termed method B.

Another aspect of the invention relates to the use of a compound of formula (I) or of a mixture of two or more compounds of the general formula (I), or of a stereoisomer thereof or of a mixture of two or more stereoisomers thereof, as an aroma chemical.

Another aspect of the invention relates to the use of a compound of formula (I) or a mixture of two or more compounds of formula (I) or a stereoisomer thereof or a mixture of two or more stereoisomers thereof for modifying the scent character of a fragranced composition.

Yet another aspect of the invention is an aroma chemical composition comprising a compound of formula (I) or a mixture of two or more compounds of the general formula (I) or a stereoisomer thereof or a mixture of two or more stereoisomers thereof and at least one further aroma chemical and/or a non-aroma chemical carrier, where the non-aroma chemical carrier is in particular selected from the group consisting of surfactants, oil components and solvents.

The invention also relates to a method for preparing a fragranced composition, e.g. a fragranced ready-to-use composition, or for modifying the scent character of a fragranced composition, e.g. of a fragranced ready-to-use composition, comprising incorporating a compound of formula (I) or a mixture of two or more compounds of the general formula (I) or a stereoisomer thereof or a mixture of two or more stereoisomers thereof into said composition.

The compounds of formula (I) as well as mixtures of two or more compounds of formula (I), their stereoisomers and the mixtures of their stereoisomers possess advantageous organoleptic properties, in particular a pleasant odor. Therefore, they can be favorably used as an aroma chemical for example in perfume compositions, body care compositions (including cosmetic compositions and products for oral and dental hygiene), hygiene articles, cleaning compositions (including dishwashing compositions), textile detergent compositions, compositions for scent dispensers, foods, food supplements, pharmaceutical compositions, crop protection compositions and other ready-to-use compositions.

Furthermore, the compounds of formula (I) as well as mixtures of two or more compounds of formula (I), their stereoisomers and the mixtures of their stereoisomers can provide other sensual effects, such as in particular a cooling effect.

By virtue of their physical properties, the compounds of formula (I) as well as mixtures of two or more compounds of formula (I), their stereoisomers and the mixtures of their stereoisomers have particularly good, virtually universal solvent properties for other fragrances and other customary ingredients in fragranced ready-to-use compositions such as, in particular, perfume compositions. Therefore, the compounds of formula (I) as well as mixtures of two or more compounds of formula (I), their stereoisomers and the mixtures of their stereoisomers are favorably combinable with other aroma chemicals, allowing, in particular, the creation of perfume compositions having novel advantageous sensory profiles.

Furthermore, the compounds of formula (I) as well as mixtures of two or more compounds of formula (I), their stereoisomers and the mixtures of their stereoisomers can be produced in good yields and purities by a simple synthesis which generally requires only one or two steps, starting from readily available starting compounds. Thus, the compounds of formula (I) as well as mixtures of two or more compounds of formula (I), their stereoisomers and the mixtures of their stereoisomers can be produced in large scales and in a simple and cost-efficient manner.

DETAILED DESCRIPTION OF THE INVENTION

Depending on the method of manufacturing, the compounds of the formula (I) can be present in pure form or in the form of mixtures. If the compounds of the formula (I) are prepared via a [4+2]-cycloaddition reaction, i.e. a Diels-Alder reaction, the compounds (1) can be present in the form of regio-isomer mixtures. Furthermore, the compounds of the formula (I) can be present in the form of stereoisomer mixtures, for example anti- and syn-stereoisomer mixtures that are typically formed in [4+2]-cycloaddition reactions and/or stereoisomer mixtures resulting from the presence of one or more substituents on the bi- and tricyclic carbon cycles core structure of the compounds (I).

Accordingly, the present invention relates to single pure compounds of the general formula (I) as well as to mixtures of two or more compounds of the formula (I) and/or mixtures of stereoisomers thereof.

The term "stereoisomers" encompasses optical isomers, such as enantiomers or diastereomers, the latter existing due to more than one stereogenic center in the molecule. The compounds of the formula (I) can have several stereogenic centers. Stereogenic centers may be the bridgehead carbon atoms of the bicyclic and tricyclic carbon cycles, the carbon atoms carrying the radicals $R^{1a}$, $R^{1b}$, $R^4$ and $R^{5a}$, provided that the particular radical $R^{1a}$, $R^{1b}$, $R^4$ or $R^{5a}$ is present, i.e. is not selected from hydrogen, and/or the carbon atoms carrying the radicals $R^2$, $R^{3a}$, $R^{3b}$, and $R^{5b}$, provided that the particular radical $R^2$, $R^{3a}$, $R^{3b}$, or $R^{5b}$ is present, i.e. is not selected from hydrogen and the corresponding dashed line does not represent a double bond. Furthermore, the radical X in compounds (I) may also have a stereogenic center, for example if X is selected from a group $X_2$ or $X_3$ and the radical $R^6$ in $X_2$ is not hydrogen and the radicals $R^6$ and $R^7$ in $X_3$ are different. The invention provides both the pure enantiomers or diastereomers and mixtures thereof and the use according to the invention of the pure enantiomers or pure diastereomers of the compound (1) or mixtures thereof.

The compounds (I) of the present invention can have specific stereochemical arrangements, which are mainly determined by the configuration of the double bonds of the diene and the dienophile that are used as the starting materials for their preferred manufacturing via [4+2]-cycloaddition reactions. For example, in compounds (I), the radicals $R^{1a}$ and $R^{1b}$ may have cis- or trans-configuration, which is typically determined by the configuration (E- or Z-configuration) of the double bonds of the diene starting material: If one of the double bonds of the diene has E-configuration and the other one has Z-configuration or vice versa, the radicals $R^{1a}$ and $R^{1b}$ in the resulting compounds (1) typically have a trans-configuration. On the other hand, if both double bonds of the diene have E-configuration or both have Z-configuration, the radicals $R^{1a}$ and $R^{1b}$ in the resulting compounds (I) typically have a cis-configuration. Furthermore, endo or exo [4+2]-cycloaddition products (diastereoisomers) may form. Thus, the radical X in compounds (1) can be arranged in syn- or anti-configuration to the radical $R^{1b}$.

In terms of the present invention, the term "pure enantiomer" has to be understood as a non-racemic mixture of a specific compound, where the desired enantiomer is present in an enantiomeric excess of >90% ee.

In terms of the present invention, the term "pure diastereomer" has to be understood as a mixture of the diastereomers of a specific compound, where the desired diastereomer is present in an amount of >90%, based on the total amount of diastereomers of said compound.

In the present context, the term "compound (I)" or "compound of formula (I)", when not defined as a specific stereoisomer or a specific mixture of stereoisomers, refers to the form of the compound as it is obtained in a non-stereoselective method used for its production. The term is however also used if it is not necessary or not possible to specify in more detail the stereochemistry of the compound (1).

Preferably, X represents a group $X_1$ or $X_2$. In particular, X represents a group $X_1$, and especially —(C=O)CH$_3$.

Preferably, the dashed line between the carbon atoms carrying the radicals $R^2$ and $R^{5b}$ represents a single bond.

Preferably, $R^{1a}$ is selected from hydrogen or methyl and $R^{1b}$ is hydrogen, or $R^{1a}$ together with $R^{1b}$ form a methylene or ethylene group.

More preferably, $R^{1a}$ and $R^{1b}$ are hydrogen, or $R^{1a}$ together with $R^{1b}$ form a methylene or ethylene group.

In particular, $R^{1a}$ and $R^{1b}$ are hydrogen, or $R^{1a}$ together with $R^{1b}$ form a methylene group.

Preferably, $R^2$ is methyl.

Preferably, $R^4$ is hydrogen.

Preferably, one of the radicals $R^{5a}$ and $R^{5b}$ is hydrogen while the other one is methyl. In particular, both radicals $R^{5a}$ and $R^{5b}$ are hydrogen.

Preferably, $R^6$ is methyl or ethyl, in particular methyl.

Preferably, $R^7$, if present, is methyl or ethyl, in particular methyl.

Further preferred are compounds (I), where 1, 2 or 3 radicals $R^2$, $R^{3a}$, $R^{3b}$, $R^4$, $R^{5a}$ and $R^{5b}$, independently of each other, are methyl while the others are hydrogen.

In particular, the dashed line between the carbon atoms carrying the radicals $R^2$ and $R^{5b}$ represents a single bond;

X represents a group $X_1$, and especially —(C=O)CH$_3$;
$R^2$ is methyl and
$R^6$ is methyl or ethyl, in particular methyl;
and both radicals $R^{5a}$ and $R^{5b}$ are hydrogen.

A preferred group embodiments of the present invention relates to the compounds of the general formula (I'), to their stereoisomers, to the mixtures of compounds of the formula (I') and to mixtures of stereoisomers of compounds of the formula (I').

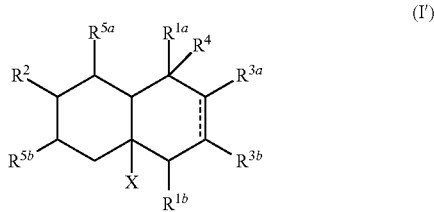
(I')

The formula (I') corresponds to formula (I), wherein the dashed line between the carbon atoms carrying the radicals $R^2$ and $R^{5b}$ represents a single bond and the dashed line between the carbon atoms carrying the radicals $R^{3a}$ and $R^{3b}$ represent a single or a double bond. In formula (I'), X, $R^{1a}$, $R^{1b}$, $R^2$, $R^{3a}$, $R^{3b}$, $R^4$, $R^{5a}$, $R^{5b}$, $R^{5b}$ and $R^{5b}$, are as defined for formula (I).

Amongst this preferred group of embodiments of the present invention preference is given to the compounds of the general formula (I'), wherein the dashed line between the carbon atoms carrying the radicals $R^{3a}$ and $R^{3b}$ represent a single or a double bond,
X represents a group of the formulae $X_1$ to $X_3$

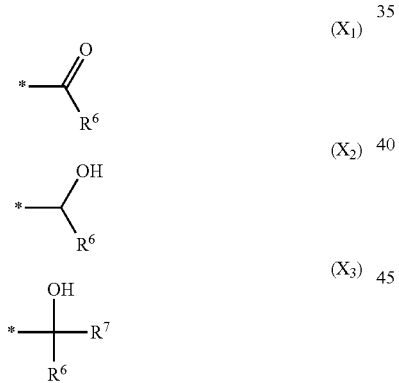

wherein the asterisk denotes the point of attachment to the rest of the molecule, and wherein X is in particular $X_1$, and especially —(C=O)CH$_3$;
$R^{1a}$ is selected from hydrogen or methyl and
$R^{1b}$ is hydrogen or
$R^{1a}$ together with $R^{1b}$ form a methylene or ethylene group,
1, 2 or 3 radicals $R^2$, $R^{3a}$, $R^{3b}$, $R^4$, $R^{5a}$ and $R^{5b}$, independently of each other, are methyl while the others are hydrogen,
$R^6$ is methyl or ethyl, in particular methyl, and
$R^7$ is methyl or ethyl, in particular methyl,
and to the mixtures thereof, the stereoisomers thereof and the mixtures of stereoisomers thereof.

An even more preferred group of embodiments of the present invention relates to the compounds of the general formula (I')

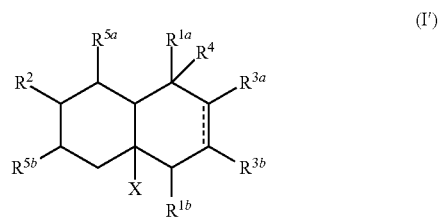
(I')

wherein
the dashed line between the carbon atoms carrying the radicals $R^{3a}$ and $R^{3b}$ represent a single or a double bond,
X is selected from —(C=O)CH$_3$ or —CH(OH)CH$_3$, in particular —(C=O)CH$_3$;
$R^{1a}$ and $R^{1b}$ are hydrogen or $R^{1a}$ together with $R^{1b}$ form a methylene or ethylene group,
$R^2$, $R^{3a}$, $R^{3b}$ and $R^4$, independently of each other, are selected from hydrogen or methyl,
$R^{5a}$ and $R^{5b}$ are hydrogen, and
$R^6$ is methyl or ethyl,
and to the mixtures thereof, the stereoisomers thereof and the mixtures of stereoisomers thereof.

A particular preferred group of embodiments of the present invention relates to compounds of the general formula (I.a), to their stereoisomers, to the mixtures of compounds of the formula (I.a) and to mixtures of stereoisomers of compounds of the formula (I.a).

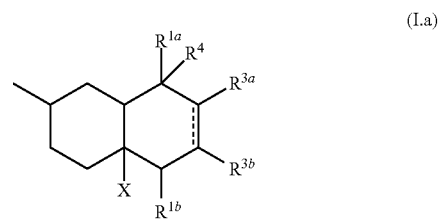
(I.a)

Formula (I.a) corresponds to formula (I'), where $R^2$ is methyl and both $R^{5a}$ and $R^{5b}$ are hydrogen. In formula (I.a) the dashed line represent a single or a double bond and the variables X, $R^{1a}$, $R^{1b}$, $R^{3a}$, $R^{3b}$, $R^4$, are as defined for formula (I) and have in particular the preferred meanings given for formulae (I) and (I') and in particular have the particularly or especially preferred meanings given in the context of formula (I').

Amongst the compounds of formula (I.a) those are particularly preferred, where
X is selected from —(C=O)CH$_3$ or —CH(OH)CH$_3$,
$R^{1a}$ and $R^{1b}$ are hydrogen, or $R^{1a}$ together with $R^{1b}$ form a methylene group, and
$R^{3a}$, $R^{3b}$ and $R^4$, independently of each other, are selected from the group consisting of hydrogen and methyl,
as well as mixtures thereof, stereoisomers thereof and mixtures of stereoisomers thereof.

A specific group of embodiment of the present invention relates to the compounds of the general formula (I.a-R), to mixtures thereof, stereoisomers thereof and mixtures of stereoisomers thereof,

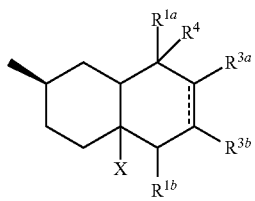

(I.a-R)

wherein
the dashed line represent a single or a double bond,
X is selected from —(C═O)CH$_3$ or —CH(OH)CH$_3$,
R$^{1a}$ and R$^{1b}$ are hydrogen, or R$^{1a}$ together with R$^{1b}$ form a methylene group, and
R$^{3a}$, R$^{3b}$ and R$^4$, independently of each other, are selected from the group consisting of hydrogen and methyl.

An even more specific embodiment of the present invention relates to the compounds of the general formula (I.a-R), to mixtures thereof, stereoisomers thereof and mixtures of stereoisomers thereof, wherein
the dashed line represent a single or a double bond,
X is selected from —(C═O)CH$_3$ or —CH(OH)CH$_3$, and is in particular —(C═O)CH$_3$,
R$^{1a}$ and R$^{1b}$ are hydrogen, or R$^{1a}$ together with R$^{1b}$ form a methylene group, and
R$^{3a}$ and R$^{3b}$, independently of each other, are hydrogen or methyl, and
R$^4$ is hydrogen.

As apparent from formula (I.a-R), the compounds of the general formula (I.a-R) have R-configuration at the carbon atom on position 2 of the hexahydro- or octahydronaphthalene framework.

As explained above in connection with the compounds of the general formula (I), the compounds of the general formulae (I.a) and (I.a-R) may have one or more further stereogenic centers. Further stereogenic center(s) may be the bridgehead carbon atoms of the bicyclic and tricyclic carbon cycles, the carbon atoms carrying the radicals R$^{1a}$, R$^{1b}$ and R$^4$, provided that the particular radical R$^{1a}$, R$^{1b}$ or R$^4$ is present, i.e. is not selected from hydrogen, and/or the carbon atoms carrying the radicals R$^{3a}$ and R$^{3b}$, provided that the particular radical R$^{3a}$ or R$^{3b}$ is present, i.e. is not selected from hydrogen, and the dashed line does not represent a double bond. Furthermore, the radical X in compounds (I.a) may also have a stereogenic center if X is selected from —CH(OH)CH$_3$. The invention provides both the pure enantiomers or diastereomers and mixtures thereof and the use according to the invention of the pure enantiomers or pure diastereomers of the compound (I.a) or mixtures thereof.

Furthermore, also the compounds of the general formulae (I.a) and (I.a-R) can have specific stereochemical arrangements, which are mainly determined by the configuration of the double bonds of the diene and the dienophile that are used as the starting materials for their preferred manufacturing via [4+2]-cycloaddition reactions. For example, in compounds (I.a) and (I.a-R), the radicals R$^{1a}$ and R$^{1b}$ typically have a trans-configuration, if one of the double bonds of the diene has E-configuration and the other one has Z-configuration or vice versa. On the other hand, the radicals R$^{1a}$ and R$^{1b}$ in the compounds (I.a) and (I.a-R) typically have cis-configuration, if both double bonds of the diene have E-configuration or both have Z-configuration. Furthermore, endo or exo [4+2]-cycloaddition products (diastereoisomers) may form. Thus, the radical X in compounds (I.a) and (I.a-R) can be arranged in syn- or anti-configuration to the radical R$^{1b}$. Apart from that, the methyl group attached to the carbon atom on position 2 of the hexahydro- or octahydro-naphthalene framework can be arranged in syn- or anti-configuration to the group X.

Examples of preferred compounds of the formulae (I), (I') and (I.a) are the compounds of the general formulae (I-1) to (I-7)

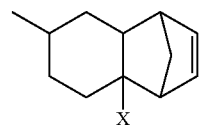
(I-1)

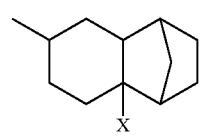
(I-2)

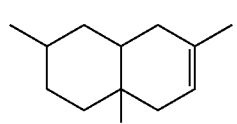
(I-3)

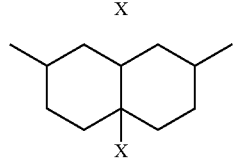
(I-4)

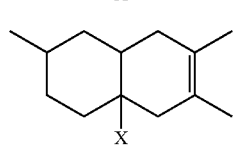
(I-5)

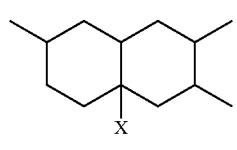
(I-6)

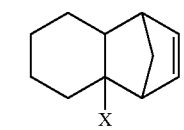
(I-7)

wherein X is as defined herein and in particular selected from the group consisting of —(C═O)CH$_3$, —CH(OH)CH$_3$ and —C(OH)(CH$_3$)$_2$.

Likewise preferred are mixtures of one or more compounds of the formulae (I-1) to (I-7), the stereoisomers of the compounds of the formulae (I-1) to (I-7) and the mixtures of two or more stereoisomers thereof.

More preferred compounds of the formulae (I), (I') and (I.a) are selected from the compounds of the general formulae (I-1) to (I-7), as defined above, wherein X is —(C═O)CH$_3$ or —CH(OH)CH$_3$.

Even more preferred compounds of the formulae (I), (I') and (I.a) are selected from the compounds of the general formulae (I-1) to (I-7), as defined above, wherein X is —(C═O)CH$_3$.

In the compounds of the formulae (I-1) to (I-7) the carbon atom of the left carbocycle, which bears the methyl group, may have R-configuration or S-configuration. Preferred are the compounds of the formulae (I-1) to (I-7) where said carbon atom has predominately R-configuration. However, mixtures of a compound of one the formulae (I-1) to (I-7), wherein said carbon atom has R-configuration, with the corresponding compound of the formulae (I-1) to (I-7), wherein said carbon atom has S-configuration, are also preferred.

Examples of preferred compounds of the formulae (I), (I') and (I.a) are selected from the compounds of the general formulae (I-1-R) to (I-6-R) and (I-7)

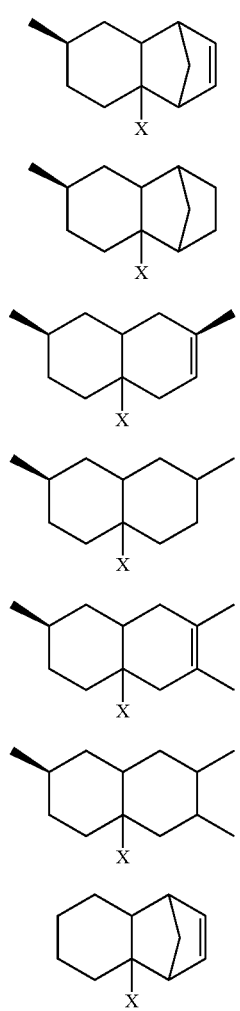

wherein X is selected from the group consisting of —(C═O)CH₃, —CH(OH)CH₃ and —C(OH)(CH₃)₂, Likewise preferred are mixtures of one or more compounds of the formulae (I-1-R) to (I-7-R), the stereoisomers of the compounds of the formulae (I-1-R) to (I-7-R) and the mixtures of two or more stereoisomers thereof.

Especially preferred compounds (I) are selected from the compounds of the general formulae (I-1-R) to (I-6-R) and (I-7), as defined above, wherein X is —(C═O)CH₃ or —CH(OH)CH₃, in particular wherein X is —(C═O)CH₃.

Examples of especially preferred compounds (I) are:
1-(7-methyl-1,5,6,7,8,8a-hexahydro-1,4-methanonaphthalen-4a(4H)-yl)ethan-1-one,
1-(7-methyloctahydro-1,4-methanonaphthalen-4a(2H)-yl) ethan-1-one,
1-(2,7-dimethyl-1,3,4,5,8,8a-hexahydronaphthalen-4a(2H)-yl)ethan-1-one,
1-(2,7-dimethyloctahydronaphthalen-4a(2H)-yl)ethan-1-one,
1-(2,6,7-trimethyl-1,3,4,5,8,8a-hexahydronaphthalen-4a(2H)-yl)ethan-1-one,
1-(2,3,7-trimethyloctahydronaphthalen-4a(2H)-yl)ethan-1-one, and
1-(1,5,6,7,8,8a-hexahydro-1,4-methanonaphthalen-4a(4H)-yl)ethan-1-one, in particular
1-((7-methyl-1,5,6,7,8,8a-hexahydro-1,4-methanonaphthalen-4a(4H)-yl)ethan-1-one,
1-(7-methyloctahydro-1,4-methanonaphthalen-4a(2H)-yl) ethan-1-one,
1-(2,7-dimethyl-1,3,4,5,8,8a-hexahydronaphthalen-4a(2H)-yl)ethan-1-one,
1-(2,7-dimethyloctahydronaphthalen-4a(2H)-yl)ethan-1-one,
1-(2,6,7-trimethyl-1,3,4,5,8,8a-hexahydronaphthalen-4a(2H)-yl)ethan-1-one, and
1-(2,3,7-trimethyloctahydronaphthalen-4a(2H)-yl)ethan-1-one.

Examples of especially preferable compounds (I) are also:
1-((7R)-7-methyl-1,5,6,7,8,8a-hexahydro-1,4-methanonaphthalen-4a(4H)-yl)ethan-1-one,
1-((7R)-7-methyloctahydro-1,4-methanonaphthalen-4a(2H)-yl)ethan-1-one,
1-((2R)-2,7-dimethyl-1,3,4,5,8,8a-hexahydronaphthalen-4a(2H)-yl)ethan-1-one,
1-((2R)-2,7-dimethyloctahydronaphthalen-4a(2H)-yl)ethan-1-one,
1-((2R)-2,6,7-trimethyl-1,3,4,5,8,8a-hexahydronaphthalen-4a(2H)-yl)ethan-1-one,
1-((7R)-2,3,7-trimethyloctahydronaphthalen-4a(2H)-yl) ethan-1-one, and
1-(1,5,6,7,8,8a-hexahydro-1,4-methanonaphthalen-4a(4H)-yl)ethan-1-one, in particular
1-((7R)-7-methyl-1,5,6,7,8,8a-hexahydro-1,4-methanonaphthalen-4a(4H)-yl)ethan-1-one,
1-((7R)-7-methyloctahydro-1,4-methanonaphthalen-4a(2H)-yl)ethan-1-one,
1-((2R)-2,7-dimethyl-1,3,4,5,8,8a-hexahydronaphthalen-4a(2H)-yl)ethan-1-one,
1-((2R)-2,7-dimethyloctahydronaphthalen-4a(2H)-yl)ethan-1-one,
1-((2R)-2,6,7-trimethyl-1,3,4,5,8,8a-hexahydronaphthalen-4a(2H)-yl)ethan-1-one, and
1-((7R)-2,3,7-trimethyloctahydronaphthalen-4a(2M-yl) ethan-1-one.

The compounds of the formula (I) can be prepared by standard methods of organic chemistry and in particular by the methods A and B as described herein.

To be more precise, the compounds of the general formula (I) can efficiently be prepared via [4+2]-cycloaddition reactions of a suitable olefinic precursor with a suitable diene precursor, under conditions of a Diels-Alder reaction. If desired, these [4+2]-cycloaddition products can, in a further step, be subjected to a selective catalytic hydrogenation reaction of the C═C double bond(s), in order to obtain a compound of the general formula (I), wherein the dashed lines represent single bonds and X represents a group X₁. Or, the [4+2]-cycloaddition products can be subjected to a complete catalytic hydrogenation reaction, where the C═C double bond(s) as well as the C═O double bond of the group X₁ are reduced in order to obtain a compound of the general formula (I), wherein the dashed lines represent single bonds and X represents a group X₂. Alternatively or in addition to the hydrogenation of the C=C double bond(s), the [4+2]-cycloaddition products comprising the group $X_1$ can be subjected to a reduction or substitution reaction, if desired, in order to convert the group $X_1$ into a group $X_2$ or $X_3$.

Step (i) of method A of the present invention comprises the reaction of diene compound of the general formula (III), as defined above, with an compound of the general formula (II), as defined above, in the presence of a catalyst, to yield a compound of the general formula (I), where the dashed line between the carbon atoms carrying the radicals $R^{3a}$ and $R^{3b}$ is a double bond and X represents a group $X_1$. Likewise, step (i') of method B of the present invention comprises the reaction of diene compound of the general formula (III'), as defined above, with an compound of the general formula (II'), as defined above, in the presence of a catalyst, to yield a compound of the general formula (I), where the dashed line between the carbon atoms carrying the radicals $R^{3a}$ and $R^{3b}$ is a double bond and X represents a group $X_1$.

Typically, steps (i) and (i') are performed under conditions of a Diels-Alder reaction, i.e. a [4+2]-cycloaddition reaction. This means for method A that the diene compound of the general formula (III) is brought in contact with the olefinic compound of the general formula (II), also referred to as "dienophile", in the presence of a suitable catalyst and typically in the presence of a non-hydrous solvent, under conditions sufficient to produce the [4+2]-cycloaddition product. This means for method B that the diene compound of the general formula (III') is brought in contact with the compound of the general formula (II'), also referred to as "dienophile", in the presence of a suitable catalyst and typically in the presence of a non-hydrous solvent, under conditions sufficient to produce the [4+2]-cycloaddition product.

In the Diels-Alder reaction, compounds containing double or triple bonds add to the 1,4-positions of a conjugated diene group with the formation of six-membered rings. The addition of the unsaturated compound to the conjugated diene is generally greatly enhanced by carbonyl groups adjacent the point of unsaturation.

The individual reaction conditions for Diels-Alder reactions are well known to the skilled person. For examples, the procedures described by H.-J. Liu et al., Can. J. Chem. 72, 1883 (1994); F. Fringuelli et al., Org. Lett. 8 (12), 2487 (2006); JOC, 51 (26), 5178 (1986); W. E. Delaney et al, WO 2012/087596 A1; T. K. M. Shing et al, Tetrahedron 60 (2004) 9179 can be applied by analogy.

Suitable catalysts that can be applied in the cycloaddition reaction in steps (i) and (i'), respectively, are typically Lewis acids, such as aluminum, zinc and titanium halides, which can be applied in unsupported or supported form. A suitable supported Lewis acid can for example be $AlCl_3$ on silica.

The amount of catalyst used in the reaction in steps (i) and (i') is typically in the range of from 0.001 to 1 equivalents, preferably in the range of from 0.01 to 0.5 equivalents, based on 1 equivalent of the compounds of the formulae (II) and (II'), respectively.

The ratio of the compound of formulae (II) and (II'), respectively, to the diene compounds of formulae (III) and (III') respectively, reacted in the reaction in steps (i) and (i'), respectively, is typically in the range of from 1:0.9 to 1:10, preferably in the range of from 1:1 to 1:5.

The reaction in steps (i) and (i') is typically carried out in the presence of an inert solvent, i.e. a solvent that does not react with the starting materials, intermediates and reagents applied in the Diels-Alder reaction or with the obtained products. Suitable solvents are for example aromatic and substituted aromatic hydrocarbons, such as benzene, chlorobenzene, dichlorobenzenes, toluene, xylene; and aliphatic hydrocarbons, such as pentane, hexanes, cyclohexane, heptanes, octanes, nonanes, decanes, ligroin and petrol ether, halogenated aliphatic hydrocarbons, such as dichloromethane, trichloromethane and tetrachloromethane, ethers, such as dibutyl ether, tetrahydrofurane (THF=, 1,4-dioxane, 1,2-dimethoxyethane; as well as mixtures thereof.

The reaction temperature applied in the cycloaddition reaction in steps (i) and (i'), respectively, is generally from 0 to 100° C., preferably from 10 to 70° C.

In this way a compound of the general formula (I), where the dashed line between the carbon atoms carrying the radicals $R^{3a}$ and $R^{3b}$ is a double bond and X represents a group $X_1$, is obtained.

These cyclisation products obtained in steps (i) and (i'), respectively, of the process according to the present invention can be obtained in pure form or in the form of product mixtures. Often, the cyclisation products of steps (i) and (i'), respectively, are obtained in the form of region- and/or stereoisomer mixtures, because the olefin can arrange itself in different ways to the dienophile during the cycloaddition reaction. The arrangement of the olefin to the dienophile highly depends on the presence and the nature of the substituents on the carbon-atoms of the C=C double bond of the compounds (II)/(II') and/or the presence and nature of the substituents on the 1,4-carbon atoms of the conjugated diene system of the diene (III)/(III').

If stereoisomer mixtures are obtained, these are typically anti- and syn-stereoisomer mixtures, i.e. diastereoisomer mixtures that are commonly formed in Diels-Alder reactions. If desired, these product mixtures can be further subjected to a purification step in order to obtain pure region- and/or stereoisomers. Such purifications can for example be performed by using chromatographic methods, by crystallization and/or by distillation, if applicable.

In steps (ii.a) and (ii'.a), respectively, the C=C double bond(s) of the compound obtained in step (i) and (i'), respectively, i.e. a compound or a mixture of compounds of formula (I), wherein the dashed line between the carbon atoms carrying the radicals $R^{3a}$ and $R^{3b}$ is a double bond and X represents a group $X_1$, are selectively hydrogenated with hydrogen in the presence of a hydrogenation catalyst, in order to obtain a compound or a mixture of compounds of the general formula (I), wherein the dashed lines represent single bonds and X represents a group $X_1$.

Suitable methods for selective hydrogenation of the C=C bond in unsaturated aldehydes and ketones without affecting the carbonyl group are well known, e.g. from P. Gallezot et al. in Catal. Rev.—Sci. Eng. 40 (1&2), (1998) pp. 81-126 and the literature cited therein; P. Claus, Topics in Catalysis 5, (1998), pp. 51-62 and the literature cited therein, V. Pandarus et al., Org. Process Res. Dev., 2012, 16, 1230; J. P. Camarena-Diaz et al., Organometallics, 2019, 38, 844; J. Ishiyama et al., Chem Lett. (1983), 8, 1234; P. Gosselin et al., Tetrahedron, 2001, 57 (4), 733.

Typically, the selective hydrogenation in steps (ii.a) and (ii'.a), respectively, is carried out in liquid phase with hydrogen in the presence of a heterogeneous hydrogenation catalyst. The heterogeneous hydrogenation catalyst and the reaction conditions are chosen such that the carbonyl group is not affected.

Suitable hydrogenation catalysts that can be applied in the selective hydrogenation of steps (ii.a) and (ii'.a), respectively, are those customarily used for the selective hydrogenation of C=C double bonds in the presence of carbonyl groups. The heterogeneous hydrogenation catalysts preferably comprise at least one metal of group VIII. Suitable metals of group VIII are selected from the group consisting of ruthenium, cobalt, rhodium, nickel, palladium and platinum, preferably form the group consisting of ruthenium, nickel, palladium and platinum. The heterogeneous hydrogenation catalysts especially comprise palladium as the catalytically active species.

Preferably, the heterogeneous hydrogenation catalysts that can be applied in steps (ii.a) and (ii'.a), respectively, are supported heterogeneous hydrogenation catalyst. The support may be any of a variety of materials on which a catalytically active material may be coated. Typically support materials are preferred, which have a rather high surface area and which are stable under the applied reaction and, if required, the applied regeneration conditions. Suitable materials are, for example, mineral materials, for example natural and synthetic minerals, metal oxides, glasses or ceramics, carbon, for example activated carbon or carbon black, plastics, for example synthetic or natural polymers, or combinations thereof. Preferred support materials are for example activated carbon, silicon dioxide, in particular amorphous silicon dioxide, alumina, titanium dioxide, chromium dioxide, and also the sulfates and carbonates of the alkaline earth metals, such as calcium carbonate, calcium sulfate, magnesium carbonate, magnesium sulfate, barium carbonate and barium sulfate. The supported heterogeneous hydrogenation catalyst may be used in the form of powders, particles, pellets, monoliths, honeycombs, packed beds, foams, aerogels, granules, beads, pills, cylinders, trilobes, extrudates, spheres or other rounded shapes, or in the form of other manufactured configurations.

The reaction temperature is generally from 10 to 120° C., preferably from 20 to 100° C., in particular from 30 to 90° C. The hydrogen pressure is generally from 2 to 100 bar absolute (0.2 to 10 MPa), preferably from 5 to 50 bar absolute (0.5 to 5 MPa). The hydrogenation can be carried out in a variety of reactors known for this purpose. Preference is given to fixed bed reactors, in particular to trickle bed reactors.

The hydrogenation reaction can be carried out in the presence or the absence of an inert solvent. Preferably, the hydrogenation reaction is carried carried out in the presence of an inert solvent. Suitable inert solvent are for example alcohols, such as methanol, ethanol, propanol and isopropanol; aromatic and substituted aromatic hydrocarbons, such as benzene, chlorobenzene, dichlorobenzenes, toluene, xylene; and aliphatic hydrocarbons, such as pentane, hexanes, cyclohexane, heptanes, octanes, nonanes, decanes, ligroin and petrol ether, halogenated aliphatic hydrocarbons, such as dichloromethane, trichloromethane and tetrachloromethane, ethers, such as dibutyl ether, THF, 1,4-dioxane, 1,2-dimethoxyethane; as well as mixtures thereof.

In steps (ii.b) and (ii'.b), respectively, the C=C double bond(s) as well as the C=O double bond of the product obtained in steps (i) and (i'), respectively, i.e. a compound or a mixture of compounds of formula (I), wherein the dashed line between the carbon atoms carrying the radicals $R^{3a}$ and $R^{3b}$ is a double bond and X represents a group $X_1$, are hydrogenated with hydrogen in the presence of a hydrogenation catalyst, in order to obtain a compound or a mixture of compounds of the general formula (I), wherein the dashed lines represent single bonds and X represents a group $X_2$.

The hydrogenation can be performed by analogy to the methods described in EP 1318131 or WO 2006/056435.

In steps (iii.a) and (iii.a'), respectively, the compound obtained in step (i) and (i'), respectively, or the compound obtained in step (ii.a) and (ii.a'), respectively, i.e. compounds of the general formula (I), wherein the dashed lines independently of each other represent a single or a double bond and X represents a group $X_1$, are subjected to a (selective) reduction reaction of the carbonyl group to a hydroxyl group, in order to obtain a compound of the general formula (I), wherein the dashed lines independently of each other represent a single or a double bond and X represents a group $X_2$.

Suitable methods for reduction of the carbonyl group to obtain an alcohol or the selective reduction of a carbonyl group in the presence of C=C double bonds in order to obtain allyl alcohols are well known to the skilled person. The reduction of the carbonyl group may be achieved e.g. by reacting the compound obtained in step (i) and (i'), respectively, or the compound obtained in steps (ii.a) and (ii'.a), respectively, wherein X represents a group $X_1$, with a boron hydride such as lithium, sodium or potassium tetrahydroborate or with an aluminum hydride such as lithium aluminum hydride. The reaction can be performed e.g. by analogy to the method described by S. Krishnamurthy et al. Org. Chem., 1977, 42(7), pp 1197-1201, J. C. Fuller et al. Tetrahedron Lett. 34, 1993, 257-260, B. Zeynidazeh et al. Bull. Korean Chem. Soc. 24 (3), 2003, 295-298. The reduction of the carbonyl group may, however, also be achieved by reacting the compound obtained in step (i) or the compound obtained in step (ii.a), respectively, wherein X represents a group $X_1$, with hydrogen in the presence of a transition metal catalyst, e.g. by analogy to the method described in EP 71787.

Alternatively, in steps (iii.b) and (iii.b'), respectively, the compound obtained in steps (i) and (i'), respectively, or the compound obtained in steps (ii.a) and (ii'.a), respectively, i.e. compounds of the general formula (I), wherein the dashed lines independently of each other represent a single or a double bond and X represents a group $X_1$, are subjected to a nucleophilic substitution reaction with a methyl nucleophile or an ethyl nucleophile, in order to obtain a compound of the general formula (I), where the dashed lines independently of each other represent a single or a double bond and X represents a group $X_3$.

Typically, in step (iii.b) and (iii.b'), respectively, of the process of the present invention, the methyl nucleophile or the ethyl nucleophile is a metal organic reagent having a metal bound alkyl radical radical $R^{7a}$ of formula $R^{7a}M$, wherein $R^{7a}$ is methyl or ethyl, and M is a metal atom or a metal halide radical, e.g. a lithium atom or a magnesium halide radical, such as MgCl, MgBr or MgI. The reaction can be performed by analogy to well-known processes of reacting carbonyl groups with metal organic compounds $R^{7a}M$, such as under the conditions of a Grignard Reaction—see e.g. K. Nutzel, et al. Methoden Org Chem (Houben Weyl) 1973, Vol. 13/2a, pp. 49-527; J. C. Stowell, Chem. Rev. 1984, 84, 409-435, H. M. Walborsky, Acc. Chem. Res. 1990, 23, 286-293, J. F. Garst, Acc. Chem. Res. 1991, 24, 95-97, A. Furstner, Angew. Chem. Int. Ed. Engl. 1993, 32, 164-189 and the references cited therein.

Generally, the reaction mixtures obtained in steps (i), (i'), (ii.a), (ii'.a), (ii.b), (ii'.b), (iii.a), (iii.b), (iii.b), and/or (iii'.b) are worked up in a customary manner, for example by mixing with water and neutralizing the reaction mixture, if acids, such as Lewis acids, bases and/or metal organic reagents were applied in the reactions, separating the phases, isolating the product from the organic phases and, if appropriate, purifying the crude products by usual methods, e.g. by distillative, extractive or chromatographic methods. If the reaction is not run in the presence of a heterogeneous catalyst, e.g. a supported Lewis-acid catalyst or a heterogeneous hydrogenation catalyst, the catalyst is typically filtered off prior to work up.

The compounds of the general formulae (II) and (II') and the diene compounds of the general formulae (III) and (III'), which are used as starting materials in the [4+2]-cycloaddition reaction in steps (i) and (i'), respectively, of the present process, are either commercially available or they can be prepared from readily available precursors by using processes that are well described in the art.

For example, the compounds of the formula (II), wherein X' is a radical $X_1$ can be prepared by the following reaction sequence depicted in scheme 1a:

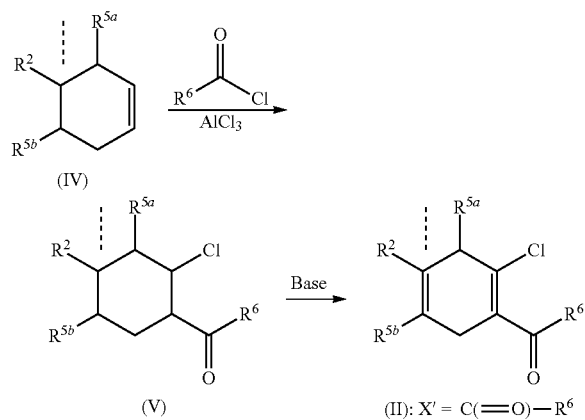

Likewise a compound of the formula (II'), wherein X' is a radical $X_1$ can be prepared by the following reaction sequence depicted in scheme 1 b:

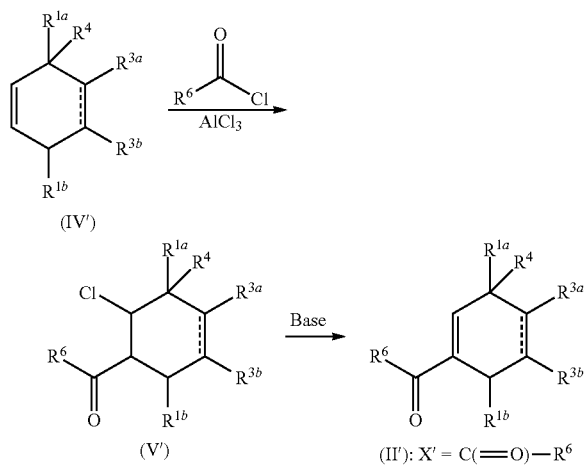

Suitable methods for carrying out the reaction sequences depicted in schemes 1a and 1b are described, for example, by Gadzhiev et al., Azerbaidzhanskii Khimicheskii Zhurnal (2005), (2) pp. 63-66.

The compounds of formula (I) as well as the mixtures of two or more compounds of formula (I), the stereoisomers thereof and the mixtures of stereoisomers thereof, as defined above, are useful as aroma chemicals.

Accordingly, a further aspect of the present invention is the use of a compound of formula (I) or of a mixture of two or more compounds of the general formula (I), or of a stereoisomer thereof or of a mixture of two or more stereoisomers thereof, as defined above, as an aroma chemical.

The term "aroma chemical" denotes a substance which is used to obtain a sensory impression, to be more precise an olfactory or flavor impression, in particular a fragrance or flavor impression. The term "olfactory" denotes an odor impression without any positive or negative judgement, while the term "fragrance" (also termed "perfume" or "scent") is connected to an odor impression which is generally felt as pleasant. A flavor induces a taste impression.

"Pleasant odor", "pleasant odor impression", "pleasant odiferous properties" are hedonistic expressions which describe the niceness and conciseness of an odor impression conveyed by an aroma chemical. The more general hedonistic expressions "advantageous sensory properties" or "advantageous organoleptic properties" describe the niceness and conciseness of an organoleptic impression conveyed by an aroma chemical. "Niceness" and "conciseness" are terms which are familiar to the person skilled in the art, a perfumer. Niceness generally refers to a spontaneously brought about, positively perceived, pleasant sensory impression. However, "nice" does not have to be synonymous with "sweet". "Nice" can also be the odor of musk or sandalwood. "Conciseness" generally refers to a spontaneously brought about sensory impression which—for the same test panel—brings about a reproducibly identical reminder of something specific. For example, a substance can have an odor which is spontaneously reminiscent of that of an "apple": the odor would then be concisely of "apples". If this apple odor were very pleasant because the odor is reminiscent, for example, of a sweet, fully ripe apple, the odor would be termed "nice". However, the odor of a typically tart apple can also be concise. If both reactions arise upon smelling the substance, in the example thus a nice and concise apple odor, then this substance has particularly advantageous sensory properties.

The term "odor-intensive substances" refers to substances or aroma chemicals exhibiting intense odor impressions. Intense odor impressions are to be understood as meaning those properties of aroma chemicals which permit a striking perception even in very low gas space concentrations. The intensity can be determined via a threshold value determination. A threshold value is the concentration of a substance in the relevant gas space at which an odor impression can just still be perceived by a representative test panel, although it no longer has to be defined. A substance class which probably belongs to the most odor-intensive known substance classes, i.e. has very low odor threshold values, are thiols, whose threshold value is often in the ppb/m$^3$ range.

Preferably, the compounds of formula (I) as well as the mixtures of two or more compounds of formula (I), the stereoisomers thereof and the mixtures of stereoisomers thereof, as defined above, are used as a fragrance.

In particular, 1-((7R)-7-methyl-1,5,6,7,8,8a-hexahydro-1,4-methanonaphthalen-4a(4H)-yl)ethan-1-one is used to impart a tobacco, amber, warm and woody note; or is used to produce a scent with a tobacco, amber, warm and woody note.

In particular, 1-((7R)-7-methyloctahydro-1,4-methanonaphthalen-4a(2H)-yl)ethan-1-one is used to impart a woody and amber note; or is used to produce a scent with a woody and amber note.

In particular, 1-((2R)-2,7-dimethyl-1,3,4,5,8,8a-hexahydronaphthalen-4a(2H)-yl)ethan-1-one is used to impart a green, pepper and herbaceous note; or is used to produce a scent with a green, pepper and herbaceous note.

In particular, 1-((2R)-2,7-dimethyloctahydronaphthalen-4a(2H)-yl)ethan-1-one is used to impart a woody, warm and amber note; or are used to produce a scent with a woody, warm and amber note.

In particular, 1-((2R)-2,6,7-trimethyl-1,3,4,5,8,8a-hexahydronaphthalen-4a(2H)-yl)ethan-1-one is used to impart a rubbery, woody and faint note; or is used to produce a scent with a rubbery, woody and faint note.

In particular, 1-((7R)-2,3,7-trimethyloctahydronaphthalen-4a(2H)-yl)ethan-1-one is used to impart a cedar and woody note; or is used to produce a scent with a cedar and woody note.

In particular, 1-(1,5,6,7,8,8a-hexahydro-1,4-methanonaphthalen-4a(4H)-yl)ethan-1-one is used to impart a herbaceous and technical note; or is used to produce a scent with a herbaceous and technical note.

The compounds of formula (I) as well as the mixtures of two or more compounds of formula (I), the stereoisomers thereof and the mixtures of stereoisomers thereof, as defined above, are generally used in a ready-to-use composition, in particular in a fragranced ready-to-use composition. "Fragranced ready-to-use composition", as used herein, refers to a ready-to-use composition which predominately induces a pleasant odor impression.

Fragranced ready-to-use compositions are for example compositions used in personal care, in home care, in industrial applications as well as compositions used in other applications, such as pharmaceutical compositions or crop protection compositions.

Preferably, the compounds of formula (I) as well as the mixtures of two or more compounds of formula (I), the stereoisomers thereof and the mixtures of stereoisomers thereof are used in a composition selected from the group consisting of perfume compositions, body care compositions (including cosmetic compositions and products for oral and dental hygiene), hygiene articles, cleaning compositions (including dishwashing compositions), textile detergent compositions, compositions for scent dispensers, foods, food supplements, pharmaceutical compositions and crop protection compositions. The compounds of formula (I) as well as the mixtures of two or more compounds of formula (I), the stereoisomers thereof and the mixtures of stereoisomers thereof are used as an aroma chemical, preferably as a fragrance, in the above compositions.

In particular, 1-((7R)-7-methyl-1,5,6,7,8,8a-hexahydro-1,4-methanonaphthalen-4a(4H)-yl)ethan-1-one is used to impart a tobacco, amber, warm and woody note to the above-listed compositions.

In particular, 1-((7R)-7-methyloctahydro-1,4-methanonaphthalen-4a(2H)-yl)ethan-1-one is used to impart a woody and amber note to the above-listed compositions.

In particular, 1-((2R)-2,7-dimethyl-1,3,4,5,8,8a-hexahydronaphthalen-4a(2H)-yl)ethan-1-one is used to impart a green, pepper and herbaceous note to the above-listed compositions.

In particular, 1-((2R)-2,7-dimethyloctahydronaphthalen-4a(2H)-yl)ethan-1-one is used to impart a woody, warm and amber note to the above-listed compositions.

In particular, 1-((2R)-2,6,7-trimethyl-1,3,4,5,8,8a-hexahydronaphthalen-4a(2H)-yl)ethan-1-one is used to impart a rubbery, woody and faint note to the above-listed compositions.

In particular, 1-((7R)-2,3,7-trimethyloctahydronaphthalen-4a(2H)-yl)ethan-1-one is used to impart a cedar and woody note to the above-listed compositions.

In particular, 1-(1,5,6,7,8,8a-hexahydro-1,4-methanonaphthalen-4a(4H)-yl)ethan-1-one is used to impart a herbaceous and technical note to the above-listed compositions.

Details to the above-listed compositions are given below.

Accordingly, another aspect of the invention relates to the use of a compounds of formula (I) or mixtures of two or more compounds of formula (I), or a stereoisomer thereof or a mixtures of stereoisomers thereof for modifying the scent character of a fragranced composition.

In addition to the olfactory properties, the compounds of formula (I) as well as the mixtures of two or more compounds of formula (I), the stereoisomers thereof and the mixtures of stereoisomers thereof exhibit advantageous secondary properties.

For example, they can provide better sensory profiles as a result of synergistic effects with other fragrances, which mean that they can provide a booster effect for other fragrances. They can therefore be used as boosters for other fragrances.

Accordingly, another aspect of the invention relates to the use of a compound of formula (I) or mixtures of two or more compounds of formula (I), or a stereoisomer thereof or a mixtures of stereoisomers thereof as a booster for other fragrances.

Booster effect means that the substances enhance and intensify in perfumery formulations the overall impression of the mixture. In the mint range, for example, it is known that menthyl methyl ether intensifies the perfumery or taste mixtures of peppermint oils and particularly in top notes brings about a considerably more intensive and more complex perception although the ether itself, being a pure substance, develops no particular intensive odor at all. In fragrance applications, Hedione® (methyl dihydrojasmonate), which as a pure substance only exhibits a light floral jasmin-note, reinforces diffusion, freshness and volume of a perfume composition as an odor booster. Booster effects are particularly desired when top-note-characterized applications are required, in which the odor impression is to be conveyed particularly quickly and intensively, for example in deodorants, air fresheners or in the taste sector in chewing gums.

To achieve such a booster effect, the compounds of formula (I) or the mixture of two or more compounds of formula (I), or the stereoisomers thereof or the mixtures of stereoisomers thereof are generally used in an overall amount of 0.1-20% by weight, preferably in an amount of 0.5 to 5% by weight, in particular in an amount of from 0.6 to 3% by weight, based on the total weight of the fragrance mixture.

Furthermore, the compounds of formula (I) as well as the mixtures of two or more compounds of formula (I), the stereoisomers thereof and the mixtures of stereoisomers thereof can have further positive effects on the composition in which they are used. For example, they can enhance the overall performance of the composition into which they are incorporated, such as the stability, e.g. the formulation stability, the extendability or the staying power of the composition.

Furthermore, the compounds of formula (I) as well as the mixtures of two or more compounds of formula (I), the stereoisomers thereof and the mixtures of stereoisomers thereof can provide other sensual effects, such as in particular a cooling effect. Accordingly these compounds are particularly suitable aroma chemicals in perfume compositions, body care compositions (in particular products for oral and dental hygiene) and hygiene articles.

In another aspect, the present invention relates to an aroma chemical composition comprising the compounds of formula (I) or a mixture of two or more compounds of formula (I), or a stereoisomer thereof or a mixture of stereoisomers thereof. The term "aroma chemical composition", as used herein, refers to a composition which induces a pleasant odor impression.

Preferably, the aroma chemical composition comprises
a compound of formula (I) or a mixture of two or more compounds of the general formula (I) or a stereoisomer thereof or a mixture of two or more stereoisomers thereof; and
at least one further aroma chemical and/or a non-aroma chemical carrier, where the non-aroma chemical carrier is in particular selected from the group consisting of surfactants, oil components and solvents.

The further aroma chemical is of course different from the compounds of formula (I) or its stereoisomers or mixtures of its stereoisomers.

By virtue of their physical properties, the compounds of formula (I) as well as the mixtures of two or more compounds of formula (I), the stereoisomers thereof and the mixtures of stereoisomers thereof have particularly good, virtually universal solvent properties for other fragrances and other customary ingredients in fragranced ready to use compositions such as, in particular, perfume compositions. Therefore, they are well combinable with other aroma chemicals, allowing, in particular, the creation of perfume compositions having novel advantageous sensory profiles. Furthermore, as already explained above, they can provide a booster effect for other fragrances.

Accordingly, in one preferred embodiment, the aroma chemical composition comprises a compound of formula (I) or a mixture of two or more compounds of formula (I), a stereoisomer thereof or a mixture of stereoisomers thereof, as defined above; and at least one further aroma chemical.

The further aroma chemical can for example be one, preferably 2, 3, 4, 5, 6, 7, 8 or further aroma chemicals, selected from the group consisting of:

Geranyl acetate (3,7-Dimethyl-2,6 octadien-1yl acetate), alpha-hexylcinnamaldehyde, 2-phenoxyethyl isobutyrate (Phenirat[1]), dihydromyrcenol (2,6-dimethyl-7-octen-2-ol), methyl dihydrojasmonate (preferably with a content of cis isomer of more than 60% by weight) (Hedione[9], Hedione HC[9]), 4,6,6,7,8,8-hexamethyl-1,3,4,6,7,8-hexahydrocyclopenta[g]benzopyran (Galaxolid[3]), tetrahydrolinalool (3,7-dimethyloctan-3-ol), ethyllinalool, benzyl salicylate, 2-methyl-3-(4-tert-butylphenyl)propanal (Lysmeral[2]), cinnamyl alcohol, 4,7-methano-3a,4,5,6,7,7a-hexahydro-5-indenyl acetate and/or 4,7-methano-3a,4,5,6,7,7a-hexahydro-6-indenyl acetate (Herbaflorati), citronellol, citronellyl acetate, tetrahydrogeraniol, vanillin, linalyl acetate, styrolyl acetate (1-phenylethyl acetate), octahydro-2,3,8,8-tetramethyl-2-acetonaphthone and/or 2-acetyl-1,2,3,4,6,7,8-octahydro-2,3,8,8-tetramethylnaphthalene (Iso E Super[3]), hexyl salicylate, 4-tert-butylcyclohexyl acetate (Oryclone[1]), 2-tert-butylcyclohexyl acetate (Agrumex HC[1]), alpha-ionone (4-(2,2,6-trimethyl-2-cyclohexen-1-yl)-3-buten-2-one), n-alpha-methylionone, alpha-isomethylionone, coumarin, terpinyl acetate, 2-phenylethyl alcohol, 4-(4-hydroxy-4-methylpentyl)-3-cyclohexenecarboxaldehyde (Lyral[3]), alpha-amylcinnamaldehyde, ethylene brassylate, (E)- and/or (Z)-3-methylcyclopentadec-5-enone (Muscenon[9]), 15-pentadec-11-enolide and/or 15-pentadec-12-enolide (Globalide[1]), 15-cyclopentadecanolide (Macrolide[1]), 1-(5,6,7,8-tetrahydro-3,5,5,6,8,8-hexamethyl-2-naphthalenyl)ethanone (Tonalid[10]), 2-isobutyl-4-methyltetrahydro-2H-pyran-4-ol (Florol[9]), 2-ethyl-4-(2,2,3-trimethyl-3-cyclopenten-1-yl)-2-buten-1-ol (Sandolen[1]), cis-3-hexenyl acetate, trans-3-hexenyl acetate, trans-2/cis-6-nonadienol, 2,4-dimethyl-3-cyclohexenecarboxaldehyde (Vertocitrali), 2,4,4,7-tetramethyloct-6-en-3-one (Claritone[1]), 2,6-dimethyl-5-hepten-1-al (Melonal[2]), borneol, 3-(3-isopropylphenyl)butanal (Florhydral[2]), 2-methyl-3-(3,4-methylenedioxyphenyl)propanal (Helional[3]), 3-(4-ethylphenyl)-2,2-dimethylpropanal (Florazon[1]), 7-methyl-2H-1,5-benzodioxepin-3(4H)-one (Calone), 3,3,5-trimethylcyclohexyl acetate (preferably with a content of cis isomers of 70% by weight) or more and 2,5,5-trimethyl-1,2,3,4,4a,5,6,7-octahydronaphthalen-2-ol (Ambrinol S[1]). Within the context of the present invention, the aforementioned aroma chemical(s) are accordingly preferably combined with the compound of formula (I) or a mixture of two or more compounds of formula (I), or a stereoisomer thereof or a mixture of stereoisomers thereof, as defined above.

Where trade names are given above, these refer to the following sources:
[1]trade name of Symrise GmbH, Germany;
[2]trade name of BASF SE;
[3]trade name of International Flavors & Fragrances Inc., USA;
[9]trade name of Firmenich S.A., Switzerland;
[10]trade name of PFW Aroma Chemicals B.V., the Netherlands.

A further embodiment of the invention relates to a composition comprising the compound of formula (I) or a mixture of two or more compounds of formula (I), or a stereoisomer thereof or a mixture of stereoisomers thereof, as defined above, and at least one further aroma chemical selected from the group consisting of methyl benzoate, benzyl acetate, geranyl acetate, 2-isobutyl-4-methyltetrahydro-2H-pyran-4-ol and linalool.

A further embodiment of the invention relates to a composition comprising the compound of formula (I) or a mixture of two or more compounds of formula (I), or a stereoisomer thereof or a mixture of stereoisomers thereof, as defined above, and 2-isobutyl-4-methyltetrahydro-2H-pyran-4-ol.

A further embodiment of the invention relates to a composition comprising the compound of formula (I) or a mixture of two or more compounds of formula (I), or a stereoisomer thereof or a mixture of stereoisomers thereof, as defined above, and methyl benzoate.

Further aroma chemicals with which the compound of formula (I) or a mixture of two or more compounds of formula (I), or a stereoisomer thereof or a mixture of stereoisomers thereof, as defined above, can be combined, e.g. to give a composition according to the invention, can be found e.g. in S. Arctander, Perfume and Flavor Chemicals, Vol. I and II, Montclair, N. J., 1969, self-published or K. Bauer, D. Garbe and H. Surburg, Common Fragrance and Flavor Materials, 4th Ed., Wiley-VCH, Weinheim 2001. Specifically, mention may be made of:
extracts from natural raw materials such as essential oils, concretes, absolutes, resins, resinoids, balsams, tinctures such as e.g.
ambergris tincture; *Amyris* oil; *Angelica* seed oil; *Angelica* root oil; aniseed oil; valerian oil; basil oil; tree moss absolute; bay oil; mugwort oil; *Benzoin* resin; bergamot oil; beeswax absolute; birch tar oil; bitter almond oil; savory oil; buchu leaf oil; *Cabreuva* oil; cade oil; calmus oil; camphor oil; *Cananga* oil; *cardamom* oil; *Cascarilla* oil; *Cassia* oil; *Cassia* absolute; *castoreum* absolute; cedar leaf oil; cedar wood oil;

*Cistus* oil; *citronella* oil; lemon oil; *Copaiba* balsam; *Copaiba* balsam oil; coriander oil; *costus* root oil; cumin oil; cypress oil; *davana* oil; dill weed oil; dill seed oil; Eau de brouts absolute; oak moss absolute; elemi oil; tarragon oil; *Eucalyptus citriodora* oil; *Eucalyptus* oil; fennel oil; pine needle oil; *galbanum* oil; *galbanum* resin; *geranium* oil; grapefruit oil; guaiacwood oil; gurjun balsam; gurjun balsam oil; *Helichrysum* absolute; *Helichrysum* oil; ginger oil; iris root absolute; iris root oil; jasmine absolute; calmus oil; camomile oil blue; roman camomile oil; carrot seed oil; *cascarilla* oil; pine needle oil; spearmint oil; caraway oil; labdanum oil; labdanum absolute; labdanum resin; lavandin absolute; lavandin oil; lavender absolute; lavender oil; lemongrass oil; lovage oil; lime oil distilled; lime oil pressed; linalool oil; *Litsea cubeba* oil; laurel leaf oil; mace oil; marjoram oil; mandarin oil; *Massoia* bark oil; *mimosa* absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; *Opopanax* oil; orange blossom absolute; orange oil; *Origanum* oil; palmarosa oil; patchouli oil; *Perilla* oil; peru balsam oil; parsley leaf oil; parsley seed oil; petitgrain oil; peppermint oil; pepper oil; pimento oil; pine oil; pennyroyal oil; rose absolute; rose wood oil; rose oil; rosemary oil; Dalmatian sage oil; Spanish sage oil; sandalwood oil; celery seed oil; spike-lavender oil; star anise oil; *styrax* oil; *tagetes* oil; fir needle oil; tea tree oil; turpentine oil; thyme oil; tolubalsam; tonka absolute; tuberose absolute; vanilla extract; violet leaf absolute; *verbena* oil; vetiver oil; juniper berry oil; wine lees oil; wormwood oil; winter green oil; hyssop oil; civet absolute; cinnamon leaf oil; cinnamon bark oil, and fractions thereof, or ingredients isolated therefrom;

individual fragrances from the group of hydrocarbons, such as e.g. 3-carene; alphapinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

the aliphatic alcohols such as e.g. hexanol; octanol; 3-octanol; 2,6-dimethylheptanol; 2-methyl-2-heptanol; 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

the aliphatic aldehydes and acetals thereof such as e.g. hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; (E/Z)-1-(1-methoxypropoxy)-hex-3-ene; the aliphatic ketones and oximes thereof such as e.g. 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

the aliphatic sulfur-containing compounds such as e.g. 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

the aliphatic nitriles such as e.g. 2-nonenenitrile; 2-undecenenitrile; 2-tridecenenitrile; 3,12-tridecadienenitrile; 3,7-dimethyl-2,6-octadienenitrile; 3,7-dimethyl-6-octenenitrile;

the esters of aliphatic carboxylic acids such as e.g. (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxy acetate; methyl-3,7-dimethyl-2,6-octadienoate; 4-methyl-2-pentyl crotonate;

the acyclic terpene alcohols such as e.g. geraniol; nerol; linalool; lavandulol; nerolidol; farnesol; tetrahydrolinalool; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

the acyclic terpene aldehydes and ketones such as e.g. geranial; neral; citronellal; 7-hydroxy-3,7-dimethyloctanal; 7-methoxy-3,7-dimethyloctanal; 2,6,10-trimethyl-9-undecenal; geranyl acetone; as well as the dimethyl- and diethylacetals of geranial, neral, 7-hydroxy-3,7-dimethyloctanal; the cyclic terpene alcohols such as e.g. menthol; isopulegol; alpha-terpineol; terpine-4-ol; menthan-8-ol; menthan-1-ol; menthan-7-ol; borneol; isoborneol; linalool oxide; nopol; cedrol; ambrinol; vetiverol; guajol; and the formates, acetates, propionates, isobutyrates, butyrates, isovalerates, pentanoates, hexanoates, crotonates, tiglinates and 3-methyl-2-butenoates thereof;

the cyclic terpene aldehydes and ketones such as e.g. menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalene-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (methyl cedryl ketone);

the cyclic alcohols such as e.g. 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols such as e.g. alpha-3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)pentan-2-ol; 3-methyl-5-(2,2,3-trimethyl-3-cyclopent-1-yl)-4-penten-2-ol; 3,3- dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers such as e.g. cineol; cedryl methyl ether; cyclododecyl methyl ether; 1,1-dimethoxycyclododecane; (ethoxymethoxy)cyclododecane; alpha-cedrene epoxide; 3a,6,6,9a-tetramethyl-dodecahydronaphtho[2,1-b]furan; 3a-ethyl-6,6,9a-trimethyldodecahydronaphtho[2,1-b]furan; 1,5,9-trimethyl-13-oxabicyclo-[10.1.0]trideca-4,8-diene; rose oxide; 2-(2,4-dimethyl-3-cyclohexen-1-yl)-5-methyl-5-(1-methylpropyl)-1,3-dioxane;

the cyclic and macrocyclic ketones such as e.g. 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 8-cyclohexadecen-1-one; 7-cyclohexadecen-1-one; (7/8)-cyclohexadecen-1-one; 9-cycloheptadecen-1-one; cyclopentadecanone; cyclohexadecanone;

the cycloaliphatic aldehydes such as e.g. 2,4-dimethyl-3-cyclohexenecarbaldehyde; 2-methyl-4-(2,2,6-trimethylcyclohexen-1-yl)-2-butenal; 4-(4-hydroxy-4-methylpentyl)-3-cyclohexene carbaldehyde; 4-(4-methyl-3-penten-1-yl)-3-cyclohexenecarbaldehyde;

the cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert-butyl (2,4-dimethyl-3-cyclohexen-1-yl) ketone;

the esters of cyclic alcohols such as e.g. 2-tert-butylcyclohexyl acetate; 4-tert-butylcyclohexyl acetate; 2-tert-pentylcyclohexyl acetate; 4-tert-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

the esters of cycloaliphatic alcohols such as e.g. 1-cyclohexylethyl crotonate;

the esters of cycloaliphatic carboxylic acids such as e.g. allyl 3-cyclohexylpropionate; allyl cyclohexyloxyacetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

the araliphatic alcohols such as e.g. benzyl alcohol; 1-phenylethyl alcohol, 2-phenylethyl alcohol, 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids such as e.g. benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

the araliphatic ethers such as e.g. 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxine; 4,4a,5,9b-tetrahydro-2,4-dimethylindeno[1,2-d]-m-dioxine;

the aromatic and araliphatic aldehydes such as e.g. benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 2-methyl-3-(4-isobutylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones such as e.g. acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylethyl)-1H5-indenyl]ethanone; 5',6',7',8'-tetrahydro-3',5',5',6',8',8'-hexamethyl-2-acetonaphthone;

the aromatic and araliphatic carboxylic acids and esters thereof such as e.g. benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds such as e.g. 2,4,6-trinitro-1,3-dimethyl-5-tert-butylbenzene; 3,5-dinitro-2,6-dimethyl-4-tert-butylacetophenone; cinnamonitrile; 3-methyl-5-phenyl-2-pentenonitrile; 3-methyl-5-phenylpentanonitrile; methyl anthranilate; methyl-N-methylanthranilate; Schiff bases of methyl anthranilate with 7-hydroxy-3,7-dimethyloctanal, 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; 2-(3-phenylpropyl)pyridine; indole; skatole; 2-methoxy-3-isopropylpyrazine; 2-isobutyl-3-methoxypyrazine;

the phenols, phenyl ethers and phenyl esters such as e.g. estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

the heterocyclic compounds such as e.g. 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

The at least one non-aroma chemical carrier can be a compound, a mixture of compounds or other additives, which have no or no noteworthy sensory properties. Typically, the at least one non-aroma chemical carrier, if present in the aroma chemical compositions according to the present invention, is a compound, a mixture of compounds or other additives, which have no or no noteworthy sensory properties. The non-aroma chemical carrier serves for the dilution and/or the fixing of the aroma chemical(s), i.e. the compounds of formula (I) and optionally one or more further aroma chemical different from compounds (I), as defined above, comprised in the aroma chemical composition.

Suitable carrier materials can be liquid or oil-like carrier materials as well as wax-like or solid carrier materials.

In particular, the non-aroma chemical carrier, if present in the compositions according to the present invention, is selected from the group consisting of surfactants, oil components and solvents.

Accordingly, a further aspect of the invention is directed to a composition comprising the compound of formula (I) or a mixture of two or more compounds of formula (I), or a stereoisomer thereof or a mixture of stereoisomers thereof, as defined above, and at least one component selected from the group consisting of surfactants, emollients (oil component) and solvents.

One embodiment of the invention is directed to a composition comprising the compound of formula (I) or a mixture of two or more compounds of formula (I), or a stereoisomer thereof or a mixture of stereoisomers thereof, as defined above, and at least one solvent.

In the context of the present invention, a "solvent" serves for the dilution of the compound of formula (I) or a mixture of two or more compounds of formula (I), or a stereoisomer thereof or a mixture of stereoisomers thereof, as defined above, to be used according to the invention without having its own odiferous properties. Some solvents have fixing properties at the same time.

The one or more solvent(s) can be present in the composition from 0.01 to 99% by weight based on the composition. In a preferred embodiment of the invention, the composition comprise 0.1 to 90 weight %, preferably 0.5 to 80 weight % of solvent(s) based on the composition. The amount of solvent(s) can be chosen depending on the composition. In one embodiment of the invention, the composition comprises 0.05 to weight %, preferably 0.1 to 5 weight %, more preferably 0.2 to 3 weight % based on the composition. In one embodiment of the invention, the composition comprises 20 to 70 weight %, preferably 25 to 50 weight % of solvent(s) based on the composition.

Preferred solvents are ethanol, dipropylene glycol (DPG), propylene glycol, 1,2-butylene glycol, glycerol, diethylene glycol monoethyl ether, diethyl phthalate (DEP), isopropyl myristate (IPM), triethyl citrate (TEC), and benzyl benzoate (BB).

Especially preferred solvents are selected from the group consisting of ethanol, propylene glycol, dipropylene glycol, triethyl citrate, benzyl benzoate and isopropyl myristate.

In a preferred embodiment of the invention, the solvent is selected from the group consisting of ethanol, isopropanol, diethylene glycol monoethyl ether, glycerol, propylene glycol, 1,2-butylene glycol, dipropylene glycol, triethyl citrate and isopropyl myristate.

According to a further aspect, the compounds of formula (I) as well as the mixtures of two or more compounds of formula (I), the stereoisomers thereof and the mixtures of stereoisomers thereof are suitable for use in surfactant-containing compositions. According to their characteristic scent profiles, they can especially be used for the perfuming of surfactant-containing compositions such as, for example, cleaners (in particular laundry care products and all-purpose cleaners).

One embodiment of the invention is therefore directed to a composition comprising the compound of formula (I) or a mixture of two or more compounds of formula (I), or a stereoisomer thereof or a mixture of stereoisomers thereof, as defined above, and at least one surfactant.

The surfactant(s) may be selected from anionic, nonionic, cationic and/or amphoteric or zwitterionic surfactants. Surfactant-containing compositions, such as for example shower gels, foam baths, shampoos, etc., preferably contain at least one anionic surfactant.

The compositions according to the invention usually contain the surfactant(s), in the aggregate, in a quantity of 0 to 40% by weight, preferably 0 to 20% by weight, more preferably 0.1 to 15% by weight, and particularly 0.1 to 10% by weight, based on the total weight of the composition. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en) yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as the N-alkyl-N,N-dimethyl ammonium glycinates, for example, cocoalkyl dimethyl ammonium glycinate, N-acylaminopropyl-N,N-dimethyl ammonium glycinates, for example, cocoacylaminopropyl dimethyl ammonium glycinate, and 2-alkyl-3-carboxymethyl-3-hydroxyethyl imidazolines, containing 8 to 18 carbon atoms in the alkyl or acyl group, and cocoacylaminoethyl hydroxyethyl carboxymethyl glycinate. The fatty acid amide derivative known under the CTFA name of Cocamidopropyl Betaine is particularly preferred.

Ampholytic surfactants are also suitable, particularly as co-surfactants. Ampholytic surfactants are surface-active compounds which, in addition to a $C_8$ to $C_{18}$ alkyl or acyl group, contain at least one free amino group and at least one —COOH— or —$SO_3H$— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalk-ylaminopropionate, cocoacylaminoethyl aminopropionate and acyl sarcosine.

Anionic surfactants are characterized by a water-solubilizing anionic group such as, for example, a carboxylate, sulfate, sulfonate or phosphate group and a lipophilic group. Dermatologically safe anionic surfactants are known to the practitioner in large numbers from relevant textbooks and are commercially available. They are, in particular, alkyl sulfates in the form of their alkali metal, ammonium or alkanolammonium salts, alkylether sulfates, alkylether carboxylates, acyl isethionates, acyl sarcosinates, acyl taurines containing linear $C_{12}$-$C_{18}$ alkyl or acyl groups and sulfosuccinates and acyl glutamates in the form of their alkali metal or ammonium salts.

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example, cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. In addition, the readily biodegradable quaternary ester compounds, such as, for example, the dialkyl ammonium methosulfates and methyl hydroxyalkyl dialkoyloxyalkyl ammonium methosulfates marketed under the name of Stepantexe and the corresponding products of the Dehyquart® series, may be used as cationic surfactants. "Esterquats" are generally understood to be quaternized fatty acid triethanolamine ester salts. They can provide the compositions with particular softness. They are known substances which are prepared by the relevant methods of organic chemistry. Other cationic surfactants suitable for use in accordance with the invention are the quaternized protein hydrolyzates.

One embodiment of the invention is directed to a composition comprising the compound of formula (I) or a mixture of two or more compounds of formula (I), or a stereoisomer thereof or a mixture of stereoisomers thereof, as defined above, and at least one oil component.

The oil components are typically present in a total quantity of 0.1 to 80, preferably 0.5 to 70, more preferably 1 to 60, even more preferably 1 to 50% by weight, in particular 1 to 40% by weight, more particularly 5 to 25% by weight and specifically 5 to 15% by weight based on the composition.

The oil components may be selected, for example, from Guerbet alcohols based on fatty alcohols containing 6 to 18 and preferably 8 to 10 carbon atoms and other additional esters, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl ole-ate, behenyl behenate, behenyl erucate, erucyl myristate, erucyl palmitate, erucyl stearate, erucyl isostearate, erucyl oleate, erucyl behenate and erucyl erucate. Also suitable are esters of $C_{18}$-$C_{38}$-alkyl-hydroxycarboxylic acids with linear or branched $C_6$-$C_{22}$-fatty alcohols, more especially dioctyl malate, esters of linear and/or branched fatty acids with polyhydric alcohols (for example propylene glycol, dimer dial or trimer triol), triglycerides based on $C_6$-$C_{10}$-fatty acids, liquid mono-, di- and triglyceride mixtures based on $C_6$-$C_{18}$-fatty acids, esters of $C_6$-$C_{22}$-fatty alcohols and/or Guerbet alcohols with aromatic carboxylic acids, more particularly benzoic acid, esters of dicarboxylic acids with polyols containing 2 to 10 car-bon atoms and 2 to 6 hydroxyl groups, vegetable oils, branched primary alcohols, substituted cyclohexanes, linear and branched $C_6$-$C_{22}$-fatty alcohol carbonates such as, for example, dicaprylyl carbonate (Cetiol® CC), Guerbet carbonates based on fatty alcohols containing 6 to 18 and preferably 8 to 10 carbon atoms, esters of benzoic acid with linear and/or branched $C_6$ to $C_{22}$-alcohols (for example Finsolv® TN), linear or branched, symmetrical or nonsymmetrical dialkyl ethers containing 6 to 22 carbon atoms per alkyl group such as, for example, dicaprylyl ether (Cetiol® OE), ring opening products of epoxidized fatty acid esters with polyols and hydrocarbons or mixtures thereof.

The compounds of formula (I) as well as the mixtures of two or more compounds of formula (I), the stereoisomers thereof and the mixtures of stereoisomers thereof, as defined above, can be used in a wide range of aroma chemical compositions. The olfactory properties, the substance properties (such as solubility in customary solvents and compatibility with further customary constituents of such compositions), as well as the toxicological acceptability of the compounds of formula (I) as well as the mixtures of two or more compounds of formula (I), the stereoisomers thereof and the mixtures of stereoisomers thereof underline their particular suitability for the stated use purposes and compositions.

Suitable aroma chemical compositions are for example perfume compositions, body care compositions, hygiene articles, cleaning compositions, textile detergent compositions, foods, food supplements, pharmaceutical compositions and crop protection compositions.

Perfume compositions can be selected from fine fragrances, air fresheners in liquid form, gel-like form or a form applied to a solid carrier, aerosol sprays, scented cleaners, perfume candles and oils, such as lamp oils or oils for massage.

Examples for fine fragrances are perfume extracts, Eau de Parfums, Eau de Toilettes, Eau de Colognes, Eau de Solide and Extrait Parfum.

Body care compositions include cosmetic compositions and products for oral and dental hygiene, and can be selected from after-shaves, pre-shave products, splash colognes, solid and liquid soaps, shower gels, shampoos, shaving soaps, shaving foams, bath oils, cosmetic emulsions of the oil-in-water type, of the water-in-oil type and of the water-in-oil-in-water type, such as e.g. skin creams and lotions, face creams and lotions, sunscreen creams and lotions, after-sun creams and lotions, hand creams and lotions, foot creams and lotions, hair removal creams and lotions, after-shave creams and lotions, tanning creams and lotions, hair care products such as e.g. hairsprays, hair gels, setting hair lotions, hair conditioners, hair shampoo, permanent and semi-permanent hair colorants, hair shaping compositions such as cold waves and hair smoothing compositions, hair tonics, hair creams and hair lotions, deodorants and antiperspirants such as e.g. underarm sprays, roll-ons, deodorant sticks and deodorant creams, products of decorative cosmetics such as e.g. eye-liners, eye-shadows, nail varnishes, make-ups, lipsticks and mascara, and products for oral and dental hygiene, such as toothpaste, dental floss, mouth wash, breath fresheners, dental foam, dental gels and dental strips.

Hygiene articles can be selected from joss sticks, insecticides, repellents, propellants, rust removers, perfumed freshening wipes, armpit pads, baby diapers, sanitary towels, toilet paper, cosmetic wipes, pocket tissues, dishwasher and deodorizer.

Cleaning compositions, such as e.g. cleaners for solid surfaces, can be selected from perfumed acidic, alkaline and neutral cleaners, such as e.g. floor cleaners, window cleaners, dishwashing detergents both for handwashing and machine washing use, bath and sanitary cleaners, scouring milk, solid and liquid toilet cleaners, powder and foam carpet cleaners, waxes and polishes such as furniture polishes, floor waxes, shoe creams, disinfectants, surface disinfectants and sanitary cleaners, brake cleaners, pipe cleaners, limescale removers, grill and oven cleaners, algae and moss removers, mold removers, facade cleaners.

Textile detergent compositions can be selected from liquid detergents, powder detergents, laundry pretreatments such as bleaches, soaking agents and stain removers, fabric softeners, washing soaps, washing tablets.

Food means a raw, cooked, or processed edible substance, ice, beverage or ingredient used or intended for use in whole or in part for human consumption, or chewing gum, gummies, jellies, and confectionaries.

A food supplement is a product intended for ingestion that contains a dietary ingredient intended to add further nutritional value to the diet. A dietary ingredient may be one, or any combination, of the following substances: a vitamin, a mineral, an herb or other botanical, an amino acid, a dietary substance for use by people to supplement the diet by increasing the total dietary intake, a concentrate, metabolite, constituent, or extract. Food supplements may be found in many forms such as tablets, capsules, softgels, gelcaps, liquids, or powders.

Pharmaceutical compositions comprise compositions which are intended for use in the diagnosis, cure, mitigation, treatment, or prevention of disease as well as articles (other than food) intended to affect the structure or any function of the body of man or other animals.

Crop protection compositions comprise compositions which are intended for the managing of plant diseases, weeds and other pests (both vertebrate and invertebrate) that damage agricultural crops and forestry.

The compositions according to the invention can further comprise one or more substances, such as, for example: preservatives, abrasives, anti-acne agents, agents to combat skin aging, antibacterial agents, anti-cellulite agents, anti-dandruff agents, antiinflammatory agents, irritation-preventing agents, irritation-alleviating agents, antimicrobial agents, antioxidants, astringents, sweat-inhibiting agents, antiseptics, antistatics, binders, buffers, carrier materials, chelating agents, cell stimulants, cleaning agents, care agents, hair removal agents, surface-active substances, deodorizing agents, antiperspirants, emulsifiers, enzymes, essential oils, fibers, film formers, fixatives, foam formers, foam stabilizers, substances for preventing foaming, foam boosters, fungicides, gelling agents, gel-forming agents, hair care agents, hair shaping agents, hair smoothing agents, moisture-donating agents, moisturizing substances, humectant substances, bleaching agents, strengthening agents, stain removal agents, optical brighteners, impregnating agents, soil repellents, friction-reducing agents, lubricants, moisturizing creams, ointments, opacifiers, plasticizers, covering agents, polish, shine agents, polymers, powders, proteins, refatting agents, exfoliating agents, silicones, skin-calming agents, skin-cleansing agents, skin care agents, skin-healing agents, skin lightening agents, skin-protective agents, skin-softening agents, cooling agents, skin-cooling agents, warming agents, skin-warming agents, stabilizers, UV-absorbent agents, UV filters, fabric softeners, suspending agents, skin-tanning agents, thickeners, vitamins, oils, waxes, fats, phospholipids, saturated fatty acids, mono- or polyunsaturated fatty acids, α-hydroxy acids, polyhydroxy fatty acids, liquefiers, dyes, color-protection agents, pigments, anticorrosives, polyols, surfactants, electrolytes, organic solvents or silicone derivatives.

The compounds of formula (I) as well as the mixtures of two or more compounds of formula (I), the stereoisomers thereof and the mixtures of stereoisomers thereof, as defined above, as well as the aroma chemical compositions according to the invention comprising them can also be in microencapsulated form, spray-dried form, in the form of inclusion complexes or in the form of extrusion products. The properties can be further optimized by so-called "coating" with suitable materials with regard to a more targeted release of the scent, for which purpose preferably waxy synthetic substances such as e.g. polyvinyl alcohol are used.

The microencapsulation can take place for example by the so-called coacervation method with the help of capsule materials, e.g. made of polyurethane-like substances or soft gelatin. The spray-dried perfume oils can be produced for example by spray-drying an emulsion or dispersion comprising the compounds of formula (I) or the mixtures of two or more compounds of formula (I), or the stereoisomers thereof or mixtures of stereoisomers thereof, as defined above, and composition obtainable by the above method of the invention, wherein carrier substances that can be used are modified starches, proteins, dextrin and vegetable gums. Inclusion complexes can be prepared e.g. by introducing dispersions of fragrance compositions and cyclodextrins or urea derivatives into a suitable solvent, e.g. water. Extrusion products can be produced by melting the compounds of formula (I) or the mixtures of two or more compounds of formula (I), or the stereoisomers thereof or mixtures of stereoisomers thereof, as defined above, or the composition obtainable by the above method of the invention with a suitable wax-like substance and by extrusion with subsequent solidification, optionally in a suitable solvent, e.g. isopropanol.

Generally, the total amount of the compounds of formula (I) or the mixtures of two or more compounds of formula (I), or the stereoisomers thereof or mixtures of stereoisomers thereof, in the aroma chemical compositions according to the present invention is typically adapted to the particular intended use or the intended application and can, thus, vary over a wide range. As a rule, the customary standard commercial amounts for scents are used.

The compositions according to the invention can comprise the compounds of formula (I) or the mixtures of two or more compounds of formula (I), or the stereoisomers thereof or mixtures of stereoisomers thereof, as defined above, in an overall amount of from 0.001 to 99.9% by weight, preferably from 0.01 to 90% by weight, more preferably from 0.05 to 80%, in particular from 0.1 to 60% by weight, more particularly from 0.1 to 40% by weight, e.g. from 0.1 to 10% by weight or 0.1 to 15% by weight, based on the total weight of the composition.

In one embodiment of the invention, the compositions comprise the compounds of formula (I) or the mixtures of two or more compounds of formula (I), or the stereoisomers thereof or mixtures of stereoisomers thereof, as defined above, in an overall amount of from 0.001 to 5 weight %, preferably from 0.01 to 2 weight % based on the total weight of the composition.

A further aspect of the invention is directed to a method of preparing an aroma chemical composition, in particular a fragranced composition, especially a fragranced ready-to-use composition, or for modifying the scent character of an aroma chemical composition, in particular of a fragranced composition, especially of a fragranced ready-to-use composition, comprising incorporating a compound of formula (I) or a mixture of two or more compounds of the general formula (I) or a stereoisomer thereof or a mixture of two or more stereoisomers thereof, as defined above, into said composition.

In particular, the invention is directed to a method of preparing a perfume composition, body care composition, hygiene article, cleaning composition, textile detergent composition, food, food supplement, pharmaceutical composition or crop protection composition, comprising including a compound of formula (I) or a mixture of two or more compounds of the general formula (I) or a stereoisomer thereof or a mixture of two or more stereoisomers thereof, as defined above, into said perfume composition, body care composition, hygiene article, cleaning composition, textile detergent composition, food, food supplement, pharmaceutical composition or crop protection composition.

In one embodiment the invention is directed to a method for imparting a tobacco, amber, warm and woody note to a perfume composition, body care composition, hygiene article, cleaning composition, textile detergent composition, food, food supplement, pharmaceutical composition or crop protection composition, which comprises including 1-((7R)-7-methyl-1,5,6,7,8,8a-hexahydro-1,4-methanonaphthalen-4a(4H)-yl)ethan-1-one in a perfume composition, body care composition, hygiene article, cleaning composition, textile detergent composition, food, food supplement, pharmaceutical composition or crop protection composition.

In another embodiment the invention is directed to a method for imparting a woody and amber note to a perfume composition, body care composition, hygiene article, cleaning composition, textile detergent composition, food, food supplement, pharmaceutical composition or crop protection composition, which comprises including 1-((7R)-7-methyl-octahydro-1,4-methanonaphthalen-4a(2H)-yl)ethan-1-one in a perfume composition, body care composition, hygiene article, cleaning composition, textile detergent composition, food, food supplement, pharmaceutical composition or crop protection composition.

In another embodiment the invention is directed to a method for imparting a green, pepper and herbaceous note to a perfume composition, body care composition, hygiene article, cleaning composition, textile detergent composition, food, food supplement, pharmaceutical composition or crop protection composition, which comprises including 1-((2R)-2,7-dimethyl-1,3,4,5,8,8a-hexahydronaphthalen-4a(2H)-yl)ethan-1-one in a perfume composition, body care composition, hygiene article, cleaning composition, textile detergent composition, food, food supplement, pharmaceutical composition or crop protection composition.

In another embodiment the invention is directed to a method for imparting a woody, warm and amber note to a perfume composition, body care composition, hygiene article, cleaning composition, textile detergent composition, food, food supplement, pharmaceutical composition or crop protection composition, which comprises including 1-((2R)-2,7-dimethyloctahydronaphthalen-4a(2H)-yl)ethan-1-one in a perfume composition, body care composition, hygiene article, cleaning composition, textile detergent composition, food, food supplement, pharmaceutical composition or crop protection composition.

In another embodiment the invention is directed to a method for imparting a rubbery, woody and faint note to a perfume composition, body care composition, hygiene article, cleaning composition, textile detergent composition, food, food supplement, pharmaceutical composition or crop protection composition, which comprises including 1-((2R)-2,6,7-trimethyl-1,3,4,5,8,8a-hexahydronaphthalen-4a(2H)-yl)ethan-1-one in a perfume composition, body care composition, hygiene article, cleaning composition, textile detergent composition, food, food supplement, pharmaceutical composition or crop protection composition.

In another embodiment the invention is directed to a method for imparting a cedar and woody note to a perfume composition, body care composition, hygiene article, cleaning composition, textile detergent composition, food, food supplement, pharmaceutical composition or crop protection composition, which comprises including 1-((7R)-2,3,7-trimethyloctahydronaphthalen-4a(2H)-yl)ethan-1-one in a perfume composition, body care composition, hygiene article, cleaning composition, textile detergent composition, food, food supplement, pharmaceutical composition or crop protection composition.

In another embodiment the invention is directed to a method for imparting a herbaceous and technical note to a perfume composition, body care composition, hygiene article, cleaning composition, textile detergent composition, food, food supplement, pharmaceutical composition or crop protection composition, which comprises including 1-(1,5,6,7,8,8a-hexahydro-1,4-methanonaphthalen-4a(4H)-yl) ethan-1-one in a perfume composition, body care composition, hygiene article, cleaning composition, textile detergent composition, food, food supplement, pharmaceutical composition or crop protection composition.

The invention is illustrated by the following examples.

EXAMPLES

Abbreviations:
 GC: gas chromatography
 MTBE: methyl tert.-butyl ether
 EtOAc: ethyl acetate
Analytics:
 The purity and identity of the products was determined by GC, $^1$H-NMR (CDCl$_3$, 500 MHz) and/or $^{13}$C-NMR (125 MHz, CDCl$_3$).

1. PREPARATION EXAMPLES

1.1 Preparation of 1-((2R)-2,6,7-trimethyl-1,3,4,5,8,8a-hexahydronaphthalen-4a(2H)-yl)ethan-1-one In a 500 mL three-necked round-bottom flask equipped with a thermometer and a 250 ml-dropping funnel, 15 g (108.5 mmol) of 1-[(4R)-4-methylcyclohexen-1-yl]ethanone was combined with AlCl$_3$ (1.5 g), and toluene (200 mL). A solution of 2,3-dimethyl-1,3-butadiene (18.2 g, 221.6 mmol) in toluene (100 mL) was added slowly through the dropping funnel over 4 hours. The reaction was stirred for another 48 hours room temperature. Water (100 mL) was added to the reaction mixture to quench it and acetic acid (50%) was added until all the gel-like materials dissolved. MTBE (100 mL) was added and followed by phase separation. Another 100 mL of MTBE was used to extract aqueous phase again. The combined organic phases were washed with water/brine (1/1, 100 mL) again followed by neutralization with Na$_2$CO$_3$ (10%) until the pH of 8. The organic phase was dried with Na$_2$SO$_4$ solid. Concentration after filtration gave 32 g of crude product. Pure product was obtained through column chromatography (Silica gel, EtOAc/hexane) as the colorless liquid with the yield of 13 g. The identity of the product was confirmed by $^1$H-NMR and $^{13}$C-NMR.

$^1$H-NMR (CDCl$_3$, 500 MHz): δ 1.69 (d, J=6.5 Hz, 3H, —CH$_3$), 0.88-0.95 (m, 1H, —CH—), 1.15-1.20 (m, 1H, —CH—), 1.42-1.51 (m, 2H, —CH$_2$—), 1.59 (s, J=11 Hz, 6H, —CH$_3$), 1.62-1.79 (m, 4H, —CH$_2$—), 1.88-2.01 (m, 4H, —CH$_2$—), 2.14 (d, J=2.5 Hz, 3H, —CH$_3$). $^{13}$C-NMR (125 MHz, CDCl$_3$): δ 18.7, 18.9, 21.6, 24.8, 26.0, 28.0, 31.2, 31.3, 34.2, 36.1, 39.4, 51.1, 121.4, 124.0, 213.7.

1.2 Preparation of 1-((7R)-2,3,7-trimethyloctahydronaphthalen-4a(2H)-yl)ethan-1-one In a 500 mL autoclave Parr reactor, 3.1 g (14.1 mmol) of the Diels-Alder adduct of example 1.1, Pd(C) (150 mg), and MeOH (50 mL) were combined. The reactor was then charged with hydrogen to the pressure of 30 bar. The reaction was monitored by GC, keeping the reaction stirring at room temperature for 36 hours and 50-60° C. for another 3 hours. The reaction mixture was filtered through celite and concentrated to give 2.6 g of crude, reduced product.

Pure product was obtained through column chromatography (Silica gel, EtOAc/hexane) as the colorless liquid with the yield of 0.7 g as the mixture of two diastereoisomers. The identity of the product was confirmed by $^1$H-NMR and $^{13}$C-NMR.

Mixture of two major isomers: $^1$H-NMR (CDCl$_3$, 500 MHz): δ 0.71-0.91 (m, 9H, —CH$_3$), 0.93-1.02 (m, 2H, —CH$_2$—), 1.08-1.58 (m, 9H, —CH—, —CH$_2$—), 1.70-1.89 (m, 3H, —CH$_2$—, —CH—), 2.12 (s, 3H, —CH$_3$).

$^{13}$C-NMR (125 MHz, CDCl$_3$): δ 11.5, 16.4, 19.4, 19.7, 19.8, 22.6, 24.6, 24.7, 26.0, 26.1, 26.8, 26.9, 27.0, 28.3, 29.5, 32.8, 33.0, 33.8, 34.9, 35.6, 37.0, 37.1, 37.9, 37, 94, 39.0, 44.2, 52.7, 52.9, 214.1, 224.1.

1.3 Preparation of 1-((2R)-2,7-dimethyl-1,3,4,5,8,8a-hexahydronaphthalen-4a(2H)-yl)ethan-1-one 1-((2R)-2,7-dimethyl-1,3,4,5,8,8a-hexahydronaphthalen-4a(2H)-yl)ethan-1-one was prepared according to example 1.1, except that 1-[(4R)-4-methylcyclohexen-1-yl]ethanone was reacted with 2-methyl-1,3-butadiene. The identity of the product was confirmed by $^1$H-NMR and $^{13}$C-NMR.

$^1$H-NMR (CDCl$_3$, 500 MHz): δ 0.85 (d, J=8.5 Hz, 3H, —CH$_3$), 0.91-0.98 (m, 1H, —CH—), 1.16-1.27 (m, 2H, —CH$_2$—), 1.41-1.53 (m, 2H, —CH$_2$—), 1.56-1.60 (m, 1H, —CH—), 1.63 (s, 3H, —CH$_3$), 1.67-1.76 (m, 2H, —CH$_2$—), 1.87-1.92 (m, 2H, —CH$_2$—), 2.03-2.10 (m, 1H, —CH—), 2.15 (s, 3H, —CH$_3$), 2.37 (m, 1H, —CH—), 5.24-5.26 (m, 1H, —CH=).

$^{13}$C-NMR (125 MHz, CDCl$_3$): δ 21.6, 23.3, 24.8, 26.0, 28.0, 30.9, 31.3, 31.6, 32.4, 36.2, 50.0, 116.9, 132.4, 213.8.

1.4 Preparation of 1-((2R)-2,7-dimethyloctahydronaphthalen-4a(2H)-yl)ethan-1-one 1-((2R)-2,7-dimethyloctahydronaphthalen-4a(2H)-yl)ethan-1-one was prepared from the reaction product obtained in example 1.3 by using the reaction procedure as described in example 1.2. The desired product was obtained as a mixture of two major isomers. The identity of the product was confirmed by $^1$H-NMR and $^{13}$C-NMR.

Major isomer: $^1$H-NMR (CDCl$_3$, 500 MHz): δ 0.76 (d, J=6.5 Hz, 3H, —CH$_3$), 0.90 (d, J=6.5 Hz, 3H, —CH$_3$), 1.04-1.21 (m, 3H, —CH—, —CH$_2$—), 1.28-1.41 (m, 4H, —CH$_2$—), 1.47-1.64 (m, 5H, —CH$_2$—, —CH—), 1.70-1.82 (m, 2H, —CH$_2$—), 2.13 (s, 3H, —CH$_3$), 2.20-2.23 (m, 1H, —CH—).

$^{13}$C-NMR (125 MHz, CDCl$_3$): δ 22.5, 22.6, 24.7, 26.1, 26.2, 30.0, 32.7, 32.8, 35.2, 35.5, 36.5, 38.3, 51.7, 214.5.

1.5 Preparation of 1-((7R)-7-methyl-1,5,6,7,8,8a-hexahydro-1,4-methanonaphthalen-4a(4H)-yl)ethan-1-one 1-((7R)-7-methyl-1,5,6,7,8,8a-hexahydro-1,4-methanonaphthalen-4a(4H)-yl)ethan-1-one was prepared according to example 1.1, except that 1-[(4R)-4-methylcyclohexen-1-yl]ethanone was reacted with cyclopenta-1,3-diene. The desired product was obtained as the mixture of two isomers. The identity of the product was confirmed by $^1$H-NMR and $^{13}$C-NMR.

Major isomer: $^1$H-NMR (CDCl$_3$, 500 MHz): δ 0.55-0.60 (m, 1H, —CH—), 0.86 (dd, J=7.0 Hz, J=1.5 Hz, 3H, —CH$_2$—), 1.00-1.06 (m, 1H, —CH—), 1.12-1.18 (m, 2H, —CH$_2$—), 1.29-1.35 (m, 2H, —CH$_2$—), 1.64-1.68 (m, 2H, —CH$_3$),1.78 (d, J=13.0 Hz, 1H, —CH—), 2.21 (d, J=1.0 Hz, 3H, —CH$_3$), 2.67 (s, 1H, —CH—), 2.84-2.87 (m, 1H, —CH—), 2.92 (s, 1H, —CH—), 6.15-6.17 (m, 1H, —CH=), 6.25-6.26 (m, 1H, —CH=).

$^{13}$C-NMR (125 MHz, CDCl$_3$): δ 22.5, 25.4, 25.9, 28.0, 28.2, 33.0, 34.4, 46.8, 47.3, 50.0, 60.1, 134.6, 138.5, 212.3.

1.6 Preparation of 1-((7R)-7-methyloctahydro-1,4-methanonaphthalen-4a(2H)-yl)ethan-1-one 1-((7R)-7-methyloctahydro-1,4-methanonaphthalen-4a(2H)-yl)ethan-1-one was prepared from the reaction product obtained in example 1.5 by using the reaction procedure as described in example 1.2. The desired product was obtained as a mixture of isomers. The identity of the product was confirmed by $^1$H-NMR and $^{13}$C-NMR.

Major isomer: $^1$H-NMR (CDCl$_3$, 500 MHz): δ 0.52-0.61 (m, 1H, —CH—), 0.84-0.90 (m, 3H, —CH$_3$), 1.07-1.25 (m, 4H, —CH$_2$—), 1.34-1.43 (m, 1H, —CH—), 1.47-1.55 (m, 3H, —CH$_2$—), 1.63-1.72 (m, 4H, —CH$_2$—), 2.07-2.11 (m, 1H, —CH—), 2.12-2.14 (m, 3H, —CH$_3$), 2.29 (s, 1H, —CH—), 2.64-2.68 (m, 1H, —CH—).

$^{13}$C-NMR (125 MHz, CDCl$_3$) δ 22.1, 22.6, 23.3, 24.5, 25.3, 26.1, 28.3, 29.5, 33.1, 37.0, 41.6, 44.0, 57.6, 212.7.

1.7 Preparation of 1-(1,5,6,7,8,8a-hexahydro-1,4-methanonaphthalen-4a(4H)-yl)ethan-1-one 1-(1,5,6,7,8,8a-hexahydro-1,4-methanonaphthalen-4a(4H)-yl)ethan-1-one was prepared according to example 1.1, except that 1-(cyclohexen-1-yl)ethanone was reacted with cyclopenta-1,3-diene. The desired product was obtained as a mixture of two major isomers. The identity of the product was confirmed by $^1$H-NMR and $^{13}$C-NMR.

Mixture of two isomers (~1/1): $^1$H-NMR (CDCl$_3$, 500 MHz): δ 0.55-0.66 (m, 1H, —CH—), 0.81-0.88 (m, 1H, —CH—), 1.02-1.70 (m, 16H, —CH$_2$—, —CH—), 1.73-1.83 (m, 3H, —CH—), 2.01-2.06 (m, 1H, —CH—), 2.09 (s, 3H, —CH$_3$), 2.20 (s, 3H, —CH$_3$), 2.46 (s, 1H, —CH—), 2.69-2.74 (m, 2H, —CH—, —CH$_2$—), 2.90 (d, J=1.5 Hz, 1H, —CH—), 5.87 (dd, (m, J=3.5 Hz, J=7.0 Hz, 1H, —CH=), 6.13-6.16 (m, 2H, —CH=), 6.21 (dd, m, J=3.5 Hz, J=7.0 Hz, 1H, —CH=).

$^{13}$C-NMR (125 MHz, CDCl$_3$): δ 17.6, 18.2, 19.0, 19.2, 24.9, 25.7, 25.9, 26.3, 26.5, 28.3, 38.5, 39.0, 44.3, 46.4, 46.6, 48.0, 49.9, 50.8, 59.4, 60.0, 132.3, 134.3, 137.6, 138.9, 211.3, 212.6.

2. OLFACTORY ASSESSMENT

In order to test the quality and intensity of the odor of the compounds (I) of the present invention, scent strip tests were performed.

For this purpose, strips of absorbent paper were dipped into solution containing 1 to 10% by weight solution of the compound (1) to be tested in ethanol. After evaporation of the solvent (about 30 sec.) the scent impression was olfactively evaluated by a trained perfumer.

The results of the scent test are summarized in table 1.

TABLE 1

Results of the scent tests.

| Example no. | Compound | Description |
|---|---|---|
| 1.1 | [structure] | Rubbery, Woody, Faint |
| 1.2 | [structure] | Cedar, Woody |
| 1.3 | [structure] | Green Pepper, Herbaceous |
| 1.4 | [structure] | Woody, Warm, Amber |
| 1.5 | [structure] | Tobacco, Amber, Warm Woody |
| 1.6 | [structure] | Woody, Amber |
| 1.7 | [structure] | Herbaceous, Technical |

Advantageous Perfume Components

The compounds of examples 1.1, 1.2, 1.3, 1.4, 1.5, 1.6 and 1.7 were formulated in the perfume compositions according to tables 2 and 3. The figures in Tables 2 and 3 mean parts by weight.

TABLE 2

Perfume oil compositions 1A and 1B

|  | 1A | 1B |
|---|---|---|
| Benzoe Siam 20% | 711 | 711 |
| Rosewood Oil brasilian | 85 | 85 |
| Copaivabalm rect. | 9 | 9 |
| Linalyl-benzoate | 31 | 31 |
| 3-cis-Hexenyl-salicylate | 21 | 21 |
| Geranyl-acetate | 47 | 47 |
| Ethyl-benzoate | 12 | 12 |
| Cinnamyl-acetate | 2 | 2 |
| Benzyl-acetate | 71 | 71 |
| Methyl-anthranilate 10% | 5 | 5 |
| Bayoil St. Thomas 10% | 5 | 5 |
| Compound mixture of example 1.1 | 50 | 20 |
|  | 1050 | 1020 |

TABLE 3

Perfume oil compositions 2A and 2B

| | 2A | 2B |
|---|---|---|
| Ethyl Caproate | 1 | 1 |
| Ethyl Acetate | 1 | 1 |
| Iso Amyl Butyrate | 1 | 1 |
| Maltol or Veltol | 1 | 1 |
| Geranyl Butyrate | 2 | 2 |
| Ethyl Vanilline 10% DPG | 2 | 2 |
| Cis 3 Hexenyl Acetate | 3 | 3 |
| Allyl Caproate | 3 | 3 |
| Verdural B 10% DPG | 3 | 3 |
| Oxyphenylon | 3 | 3 |
| Hexyl Butyrate | 4 | 4 |
| Ethyl Decadienoate 10% DPG | 4 | 4 |
| DM.B.C. Butyrate | 4 | 4 |
| Ethyl Maltol or Veltol Plus | 4 | 4 |
| Cyclaprop | 5 | 5 |
| Iso Amyl Acetate | 5 | 5 |
| Cis 3 Hexenol 10% DPG | 6 | 6 |
| D.M.B.C. Acetate | 7 | 7 |
| Aldehyde C 16 100% | 8 | 8 |
| Geranyl Propionate | 8 | 8 |
| Ethyl 2 Methyl Butyrate | 8 | 8 |
| Decalactone Gamma | 10 | 10 |
| Orange Oil Brasil | 10 | 10 |
| Ethyl Aceto Acetate | 10 | 10 |
| Linalool | 15 | 15 |
| Benzyl Acetate | 15 | 15 |
| Aldehyde C 14 100% | 20 | 20 |
| Citronellol | 25 | 25 |
| Linalyl Acetate | 30 | 30 |
| Geranyl Acetate | 35 | 35 |
| Vertenex | 45 | 45 |
| Citronellyl Acetate | 50 | 50 |
| Verdox | 54 | 54 |
| Galaxolide 50 DEP | 100 | 100 |
| Hexyl Acetate | 190 | 190 |
| Compound mixture of example 1.1 | 300 | 200 |
| | 1000 | 900 |

Perfume oil composition 3 corresponds to perfume oil composition 1B, where the compound of example 1.1 is replaced by the same amount of the compound of example 1.2.

Perfume oil composition 4 corresponds to perfume oil composition 1B, where the compound of example 1.1 is replaced by the same amount of the compound of example 1.3.

Perfume oil composition 5 corresponds to perfume oil composition 1B, where the compound of example 1.1 is replaced by the same amount of the compound of example 1.4.

Perfume oil composition 6 corresponds to perfume oil composition 1B, where the compound of example 1.1 is replaced by the same amount of the compound of example 1.5.

Perfume oil composition 7 corresponds to perfume oil composition 1B, where the compound of example 1.1 is replaced by the same amount of the compound of example 1.6.

Perfume oil composition 8 corresponds to perfume oil composition 1B, where the compound of example 1.1 is replaced by the same amount of the compound of example 1.7.

Perfume oil composition 9 corresponds to perfume oil composition 2B, where the compound of example 1.1 is replaced by the same amount of the compound of example 1.2.

Perfume oil composition 10 corresponds to perfume oil composition 2B, where the compound of example 1.1 is replaced by the same amount of the compound of example 1.3.

Perfume oil composition 11 corresponds to perfume oil composition 2B, where the compound of example 1.1 is replaced by the same amount of the compound of example 1.4.

Perfume oil composition 12 corresponds to perfume oil composition 2B, where the compound of example 1.1 is replaced by the same amount of the compound of example 1.5.

Perfume oil composition 13 corresponds to perfume oil composition 2B, where the compound of example 1.1 is replaced by the same amount of the compound of example 1.6.

Perfume oil composition 14 corresponds to perfume oil composition 2B, where the compound of example 1.1 is replaced by the same amount of the compound of example 1.7.

The compound of formula (I) or the mixtures of two or more compounds of the general formula (I), or of a stereoisomer thereof or of a mixture of two or more stereoisomers thereof, in particular the compounds of examples 1.1, 1.2, 1.3, 1.4, 1.5, 1.6 or 1.7 may be used in a broad range of fragrance applications, e.g. in any field of fine and functional perfumery, such as perfumes, household products, laundry products, body care products and cosmetics. The compound of formula (I) or the mixtures of two or more compounds of the general formula (I), or of a stereoisomer thereof or of a mixture of two or more stereoisomers thereof, in particular the compounds of examples 1.1, 1.2, 1.3, 1.4, 1.5, 1.6 or 1.7, can be employed in widely varying amounts, depending upon the specific application and on the nature and quantity of other odorant ingredients. The proportion is typically from 0.001 to 20 weight percent of the application. In one embodiment, the compound of formula (I) or the mixtures of two or more compounds of the general formula (I), or of a stereoisomer thereof or of a mixture of two or more stereoisomers thereof, in particular the compounds of examples 1.1, 1.2, 1.3, 1.4, 1.5, 1.6 or 1.7, are employed in a fabric softener in an amount of from 0.001 to 0.05 weight percent. In another embodiment, the compound of formula (I) or the mixtures of two or more compounds of the general formula (I), or of a stereoisomer thereof or of a mixture of two or more stereoisomers thereof, in particular the compounds of examples 1.1, 1.2, 1.3, 1.4, 1.5, 1.6 or 1.7, are used in fine perfumery in amounts of from 0.1 to 20 weight percent, more preferably between 0.1 and 5 weight percent. However, these values are given only by way of example, since the experienced perfumer may also achieve effects or may create novel accords with lower or higher concentrations.

The compound of formula (I) or the mixtures of two or more compounds of the general formula (I), or of a stereoisomer thereof or of a mixture of two or more stereoisomers thereof, in particular the compounds of examples 1.1, 1.2, 1.3, 1.4, 1.5, 1.6 or 1.7, may be employed into the fragrance application simply by directly mixing the fragrance composition with the fragrance application, or they may, in an earlier step be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the application.

Thus, the invention additionally provides a method of manufacturing a fragrance application, comprising the incorporation of the compound of formula (I) or the mixtures of two or more compounds of the general formula (I), or of a stereoisomer thereof or of a mixture of two or more stereoisomers thereof, in particular the compounds of examples 1.1, 1.2, 1.3, 1.4, 1.5, 1.6 or 1.7, as a fragrance ingredient, either by directly admixing the compound of formula (I) or the mixtures of two or more compounds of the general formula (I), or of a stereoisomer thereof or of a mixture of two or more stereoisomers thereof, in particular the compounds of examples 1.1, 1.2, 1.3, 1.4, 1.5, 1.6 or 1.7, to the application or by admixing a fragrance composition comprising the compound of formula (I) or the mixtures of two or more compounds of the general formula (I), or of a stereoisomer thereof or of a mixture of two or more stereoisomers thereof, in particular the compounds of examples 1.1, 1.2, 1.3, 1.4, 1.5, 1.6 or 1.7, which may then be mixed to a fragrance application, using conventional techniques and methods.

As used herein, "fragrance application" means any product, such as fine perfumery, e.g. perfume and Eau de Toilette; household products, e.g. detergents for dishwasher, surface cleaner; laundry products, e.g. softener, bleach, detergent; body care products, e.g. shampoo, shower gel; and cosmetics, e.g. deodorant, vanishing creme, comprising an odorant. This list of products is given by way of illustration and is not to be regarded as being in any way limiting.

The compound of formula (I) or the mixtures of two or more compounds of the general formula (I), or of a stereoisomer thereof or of a mixture of two or more stereoisomers thereof, in particular the compounds of examples 1.1, 1.2, 1.3, 1.4, 1.5, 1.6 or 1.7, may be used as part of the perfume in the above mentioned applications. The compound of formula (I) or the mixtures of two or more compounds of the general formula (I), or of a stereoisomer thereof or of a mixture of two or more stereoisomers thereof, in particular the compounds of examples 1.1, 1.2, 1.3, 1.4, 1.5, 1.6 or 1.7, may be used alone or as part of a perfume. The term "perfume" is used synonymously to "perfume oil" or "perfume (oil) composition".

The invention claimed is:

1. A compound of the general formula (I.a)

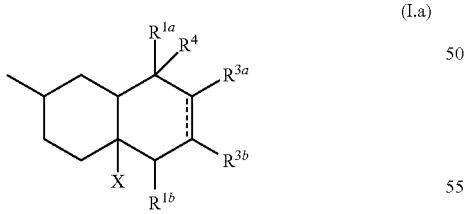

(I.a)

wherein
the dashed line represents a single or a double bond,
X is selected from the group consisting of —(C=O)CH$_3$ and —CH(OH)CH$_3$,
R$^{1a}$ and R$^{1b}$ are hydrogen, or R$^{1a}$ together with R$^{1b}$ form a methylene group, and
R$^{3a}$, R$^{3b}$ and R$^4$, independently of each other, are selected from the group consisting of hydrogen and methyl,
a mixture thereof, a stereoisomer thereof or a mixture of stereoisomers thereof; except for the compound of formula (I.a) where R$^{1a}$, R$^{1b}$, R$^{3a}$, R$^{3b}$ and R$^4$ are hydrogen, the dashed line represents a single bond and X is —(C=O)CH$_3$.

2. The compound according to claim 1, which is a compound of the general formula (I.a-R)

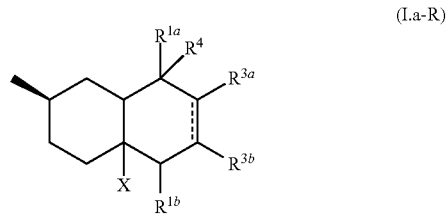

(I.a-R)

wherein
the dashed line represents a single or a double bond,
X is selected from the group consisting of —(C=O)CH$_3$ and —CH(OH)CH$_3$,
R$^{1a}$ and R$^{1b}$ are hydrogen, or R$^{1a}$ together with R$^{1b}$ form a methylene group, and
R$^{3a}$, R$^{3b}$ and R$^4$, independently of each other, are selected from the group consisting of hydrogen and methyl,
a mixture thereof, a stereoisomer thereof or a mixture of stereoisomers thereof.

3. The compound according to claim 2, where the compounds of the general formula (I.a-R) have at least one of the following features a) and/or b)
a) X is —(C=O)CH$_3$,
b) R$^4$ is hydrogen.

4. A compound selected from the group consisting of compounds of the general formulae (I-1-R) to (I-6-R) and (I-7)

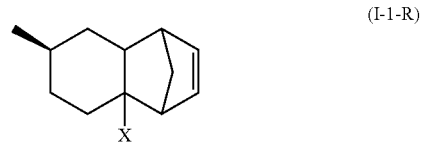

(I-1-R)

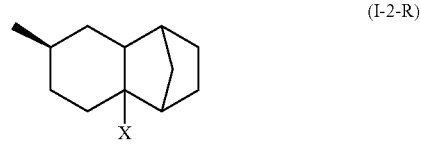

(I-2-R)

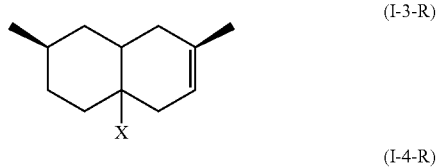

(I-3-R)

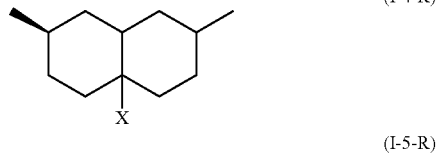

(I-4-R)

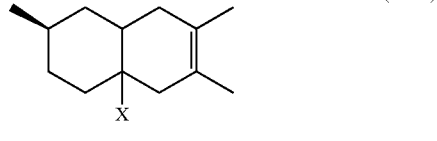

(I-5-R)

-continued

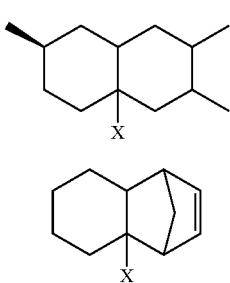

(I-6-R)

(I-7)

wherein X is selected from the group consisting of —(C=O)CH$_3$ and —CH(OH)(CH$_3$),
or of a mixture thereof, or of a stereoisomer thereof or of a mixture of two or more stereoisomers thereof.

5. The compound according to claim 4, where X is —(C=O)CH$_3$.

6. A process for preparing a compound of the general formula (I.a), or a mixture of two or more compounds of the general formula (I.a) or a stereoisomer thereof or a mixture of two or more stereoisomers thereof according to claim 1, the process comprising:

(i) reacting a compound of the general formula (II)

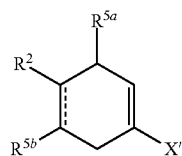

(II)

wherein
the dashed line represents a single bond,
X' represents a group of the formula X$_1$

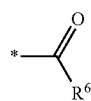

(X$_1$)

wherein the asterisk denotes the point of attachment to the rest of the molecule,
R$^2$ is hydrogen or methyl,
R$^{5a}$ and R$^{5b}$ are hydrogen, and
R$^6$ is methyl,
with a diene compound of the general formula (III)

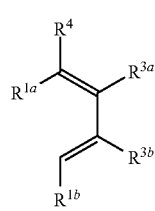

(III)

wherein
R$^{1a}$ and R$^{1b}$, independently of each other, are selected from the group consisting of hydrogen and methyl, or R$^{1a}$ together with R$^{1b}$ form a methylene group, and
R$^{3a}$, R$^{3b}$ and R$^4$, independently of each other, are selected from the group consisting of hydrogen and methyl, in the presence of a catalyst,
to yield a compound of the general formula (I.a), where the dashed line between the carbon atoms carrying the radicals R$^{3a}$ and R$^{3b}$ is a double bond and X represents a group X$_1$,
and optionally one or two of the following steps:

(ii.a) selective catalytic hydrogenation of the C=C double bond(s) of the compound obtained in step (i) with hydrogen in the presence of a hydrogenation catalyst, to obtain a compound of the general formula (I.a), wherein the dashed line represents a single bond and X represents a group X$_1$,
or (ii.b) catalytic hydrogenation of the C=C double bond(s) and the C=O double bond of the compound obtained in step (i) with hydrogen in the presence of a hydrogenation catalyst, to obtain a compound of the general formula (I.a), wherein the dashed lines represent single bonds and X represents a group —CH(OH)CH$_3$, (iii.a) subjecting the compound obtained in step (i) or the compound obtained in step (ii.a) to a reduction reaction of the carbonyl group to a hydroxyl group, to obtain a compound of the general formula (I.a), wherein the dashed lines independently of each other represent a single or a double bond and X represents a group —CH(OH)CH$_3$.

7. A process for preparing a compound of the general formula (I), or a mixture of two or more compounds of the general formula (I.a) or a stereoisomer thereof or a mixture of two or more stereoisomers thereof, according to claim 1, the process comprising:

(i') reacting a compound of the general formula (II')

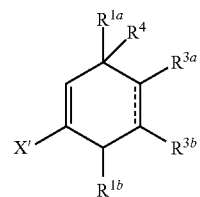

(II')

wherein
the dashed line represent a single or a double bond,
X' represents a group of the formula X$_1$

(X$_1$)

wherein the asterisk denotes the point of attachment to the rest of the molecule,
R$^{1a}$ and R$^{1b}$, independently of each other, are selected from the group consisting of hydrogen and methyl, or R$^{1a}$ together with R$^{1b}$ form a methylene group, and $R^{3a}$, $R^{3b}$ and $R^4$, independently of each other, are selected from the group consisting of hydrogen and methyl,
$R^6$ is methyl,
with a diene compound of the general formula (III')

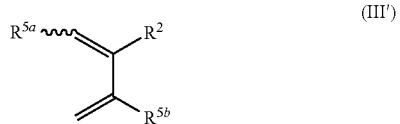

wherein
$R^2$ is hydrogen or methyl,
and
$R^{5a}$ and $R^{5b}$ are hydrogen,
in the presence of a catalyst,
to yield a compound of the general formula (I.a'), where X represents a group $X_1$, and $R^2$ is hydrogen or methyl,

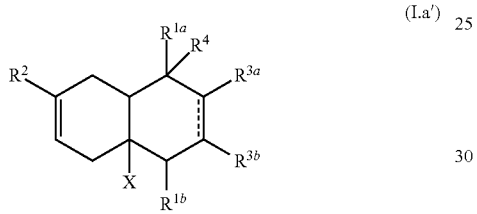

and one or two of the following steps:
(ii'.a) selective catalytic hydrogenation of the C═C double bond(s) of the compound obtained in step (i') with hydrogen in the presence of a hydrogenation catalyst, to obtain a compound of the general formula (I.a), wherein the dashed line represents a single bond and X represents a group $X_1$,
or
(ii'.b) catalytic hydrogenation of the C═C double bond(s) and the C═O double bond of the compound obtained in step (i') with hydrogen in the presence of a hydrogenation catalyst, to obtain a compound of the general formula (I.a), wherein the dashed line represents a single bond and X represents a group —CH(OH)CH$_3$,
(iii'.a) subjecting the compound obtained in step (i') or the compound obtained in step (ii'.a) to a reduction reaction of the carbonyl group to a hydroxyl group, to obtain a compound of the general formula (I.a), wherein the dashed line represents a single or a double bond and X represents a group —CH(OH)CH$_3$.

8. An aroma chemical comprising a compound of formula (I.a) or of a mixture of two or more compounds of the general formula (I.a), or of a stereoisomer thereof or of a mixture of two or more stereoisomers thereof, according to claim 1.

9. An aroma chemical composition comprising
a compound of formula (I.a) or a mixture of two or more compounds of the general formula (I.a) or a stereoisomer thereof or a mixture of two or more stereoisomers thereof, according to claim 1, and
at least one further aroma chemical and/or a non-aroma chemical carrier, where the non-aroma chemical carrier is selected from the group consisting of surfactants, oil components and solvents.

10. A method of preparing a fragranced composition, comprising incorporating a compound of formula (I.a) or a mixture of two or more compounds of the general formula (I.a) or a stereoisomer thereof or a mixture of two or more stereoisomers thereof, according to claim 1, into said composition.

11. A method for modifying the scent character of a fragranced composition, comprising incorporating a compound of formula (I.a) or a mixture of two or more compounds of the general formula (I.a) or a stereoisomer thereof or a mixture of two or more stereoisomers thereof, according to claim 1, into said fragranced composition.

* * * * *